US006227050B1

(12) United States Patent
Fujii et al.

(10) Patent No.: US 6,227,050 B1
(45) Date of Patent: *May 8, 2001

(54) SEMICONDUCTOR MECHANICAL SENSOR AND METHOD OF MANUFACTURE

(75) Inventors: Tetsuo Fujii, Toyohashi; Masahito Imai, Chita, both of (JP)

(73) Assignee: Nippondense Co., Ltd., Kariya (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/181,615

(22) Filed: Oct. 28, 1998

Related U.S. Application Data

(62) Division of application No. 08/834,129, filed on Apr. 14, 1997, now Pat. No. 5,872,024, which is a division of application No. 08/508,170, filed on Jul. 27, 1995, now Pat. No. 5,627,318, which is a division of application No. 08/109,504, filed on Aug. 20, 1993, now Pat. No. 5,461,916.

(30) Foreign Application Priority Data

| Aug. 21, 1992 | (JP) | 4-223072 |
| Oct. 12, 1992 | (JP) | 4-273202 |
| Apr. 2, 1993 | (JP) | 5-077151 |

(51) Int. Cl.[7] .............................. G01P 15/125; G01P 9/04
(52) U.S. Cl. .................................. 73/514.32; 73/504.15; 361/283.3
(58) Field of Search ............................ 73/504.15, 514.32, 73/514.16, 504.12, 504.13, 504.14; 361/307, 283.3, 321.1, 321.5, 283.1

(56) References Cited

U.S. PATENT DOCUMENTS

| 4,483,194 | 11/1984 | Rudolf . |
| 4,574,327 | 3/1986 | Wilner . |
| 4,598,585 | 7/1986 | Boxenhom . |

(List continued on next page.)

FOREIGN PATENT DOCUMENTS

| 2240178 | 7/1991 | (GB) . |
| 60244864 | 12/1985 | (JP) . |
| 61073071 | 4/1986 | (JP) . |
| 61114123 | 5/1986 | (JP) . |
| 6227666 | 2/1987 | (JP) . |
| 62207917 | 9/1987 | (JP) . |
| 3074926 | 11/1991 | (JP) . |
| WO 9322690 | 11/1993 | (WO) . |

OTHER PUBLICATIONS

Richard S. Payne et al. "Surface Micromachined Accelerometer: A Technology Update", SAE International, Feb. 25, 1991; pp. 127–135.

Primary Examiner—Helen C. Kwok
(74) Attorney, Agent, or Firm—Pillsbury Madison & Sutro LLP

(57) ABSTRACT

A semiconductor mechanical sensor having a new structure in which a S/N ratio is improved. In the central portion of a silicon substrate 1, a recess portion 2 is formed which includes a beam structure. A weight is formed at the tip of the beam, and in the bottom surface of the weight in the bottom surface of the recess portion 2 facing the same, an electrode 5 is formed. An alternating current electric power is applied between the weight portion 4 and the electrode 5 so that static electricity is created and the weight is excited by the static electricity. In an axial direction which is perpendicular to the direction of the excitation of the weight, an electrode 6 is disposed to face one surface of the weight and a wall surface of the substrate which faces the same. A change in a capacitance between the facing electrodes is electrically detected, and therefore, a change in a physical force acting in the same direction is detected.

31 Claims, 21 Drawing Sheets

U.S. PATENT DOCUMENTS

| | | |
|---|---|---|
| 4,609,968 | 9/1986 | Wilner . |
| 4,653,326 | 3/1987 | Danel et al. . |
| 4,679,434 | 7/1987 | Stewart . |
| 4,711,128 | 12/1987 | Boura . |
| 4,744,248 | 5/1988 | Stewart . |
| 4,744,249 | 5/1988 | Stewart . |
| 4,783,237 | 11/1988 | Aine et al. . |
| 4,891,984 | 1/1990 | Fujii et al. . |
| 4,922,756 | 5/1990 | Henrion ............... 73/577 R |
| 5,016,072 | 5/1991 | Greiff . |
| 5,095,752 | 3/1992 | Suzuki et al. ............ 73/514.32 |
| 5,151,763 | 9/1992 | Marek et al. . |
| 5,243,861 | 9/1993 | Kloeck et al. ............ 73/514.32 |
| 5,275,047 | 1/1994 | Zabler . |
| 5,277,053 | 1/1994 | McLane et al. ............ 73/577 B |
| 5,313,835 | 5/1994 | Dunn .................. 73/505 |
| 5,313,836 | 5/1994 | Fujii . |
| 5,329,815 | 7/1994 | Dunn .................. 73/505 |
| 5,335,544 | 8/1994 | Wagner et al. ............ 73/514.32 |
| 5,345,824 * | 9/1994 | Sherman et al. ........... 73/514.32 |
| 5,377,544 | 1/1995 | Dunn .................. 73/505 |
| 5,377,545 | 1/1995 | Norling . |
| 5,417,312 | 5/1995 | Tsuchutani et al. ......... 73/514.32 |
| 5,461,916 | 10/1995 | Fujii . |
| 5,511,419 | 4/1996 | Dunn ................ 73/504.08 |
| 5,569,852 * | 10/1996 | Marek et al. ............. 73/514.32 |
| 5,574,222 * | 11/1996 | Offenberg .............. 73/514.32 |
| 5,604,312 | 2/1997 | Lutz . |
| 5,616,312 | 4/1997 | Benz . |
| 5,627,318 | 5/1997 | Fujii .................. 73/514.32 |

\* cited by examiner

DIRECTION OF CORIOLI'S FORCE

DIRECTION OF VIBRATION DUE TO STATIC ELECTRICITY

ROTATION SHAFT

VOLTAGE Vs (INPUT WAVEFORM)

$V_s = V \cdot \sin\omega_a t$

DISPLACEMENT DUE TO CORIOLI'S FORCE $D_{FY} = K \cdot \sin 2\omega_a t$

VOLTAGE (OUTPUT WAVEFORM AT POINT α)

SAMPLE-AND-HOLD PERIOD T1    SAMPLE-AND-HOLD PERIOD T2

VOLTAGE (INPUT WAVEFORM)

TIME

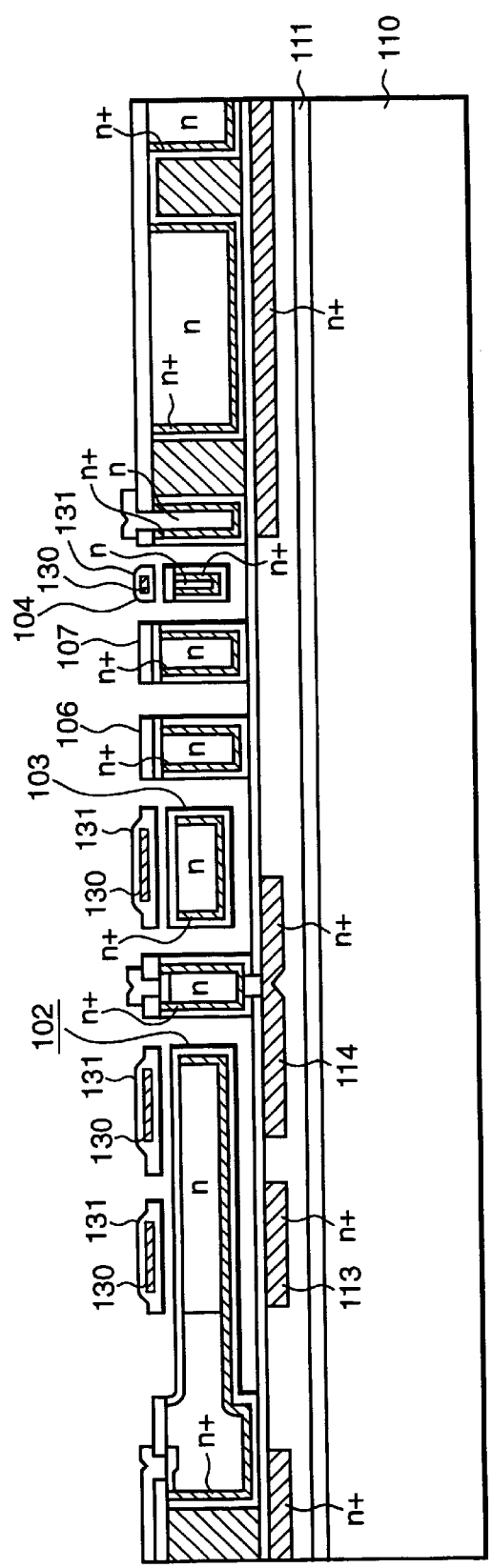

SEMICONDUCTOR MECHANICAL SENSOR AND METHOD OF MANUFACTURE

This is a division of application Ser. No. 08/834,129 filed Apr. 14, 1997, now U.S. Pat. No. 5,872,024, which was a DIV of Ser. No. 08/508,170 filed Jul. 27, 1995, now U.S. Pat. No. 5,627,318, which was a DIV of Ser. No. 08/109,504, filed Aug. 20, 1993, now U.S. Pat. No. 5,461,916.

BACKGROUND OF THE INVENTION

1. Field of the Invention

The present invention relates to a method of manufacturing a semiconductor mechanical sensor same, and more particularly, to a method for manufacturing a acceleration sensor or a yaw rate sensor.

2. Description of the Related Art

As a semiconductor mechanical sensor such as an acceleration sensor, a yaw rate sensor, or sensors using piezoelectric ceramics are in wide use for attitude control of an automobile and to prevent jitter in a commercial video camera. In addition, Japanese Patent Publication Gazette No. 3-74926 discloses that two piezoelectric resistor elements arranged in parallel to a longitudinal axis of the cantilever, and in a side-by-side configuration, detects a force which corresponds to a rotation speed. In other words, without detecting deformation due to vibration of the cantilever, only deformation due to twisting of the cantilever is detected by the piezoelectric resistor element.

However, regarding accuracy, cost, etc., existing yaw rate sensors are not satisfactory, which restricts their application to other purposes.

SUMMARY OF THE INVENTION

It is an object of the present invention to solve such a problem and to offer a semiconductor mechanical sensor having a new structure.

A further object of the present invention is to provide a method of manufacturing a sensor to improve the S/N ratio in such a semiconductor mechanical sensor having a new structure.

A still further object of the present invention is to offer a semiconductor mechanical sensor using a beam deflection type capacity detection method and a method of manufacturing the same, and to offer a semiconductor mechanical sensor which can detect mechanical changes in two or three directions (when two such semiconductor mechanical sensors are used) and a method of manufacturing the same.

To achieve these objects, basically, a semiconductor mechanical sensor according to the present invention has a structure as follows. That is, the semiconductor mechanical sensor manufactured according to the method of the present invention comprises:

a semiconductor substrate;

a beam which is formed on the semiconductor substrate, the beam having a weight; a first pair of electrodes one of which is formed on a first surface of the weight and another one of which is formed on a first surface of a wall of the substrate opposite to the same surface of the weight; and a second pair of electrodes which arranged perpendicular to the first pair of electrodes and one of which is formed on a second surface of the weight different from the first surface thereof and another one of which is formed on a second surface of a wall different from the first surface of the wall of the substrate, and opposite to the same surface of the weight.

In other aspect of the present invention, in addition to the above structure, the semiconductor mechanical sensor comprises: an AM modulation circuit for superimposing a signal from the physical force detect electrode onto a carrier wave; and a band pass filter for passing a signal from the AM modulation circuit whose center frequency coincides with the carrier wave.

In a further aspect of the present invention, a method of manufacturing such a semiconductor mechanical sensor comprises the steps of:

a first step of forming a groove of a predetermined depth in a main surface of a monocrystalline silicon substrate and perpendicular to the main surface thereof, to thereby form a beam which has a weight;

a second step of forming a pair of electrodes which face each other, one of which is provided on a side surface of the weight formed in a surface layer of the substrate and another one of which is provided on an inner surface of the groove opposite to the side surface of the weight, and forming another electrode on a surface of the weight in a direction which is perpendicular to the groove;

a third step of filling the groove with a filling material, forming an electrode on a bottom surface of the groove and opposite to the other electrode which is formed on the surface of the weight with the filling material interposed therebetween to thereby form another pair of electrodes, and of smoothing the major surface of the monocrystalline silicon substrate;

a forth step of combining the main surface of the monocrystalline silicon substrate with a separately prepared substrate;

a fifth step of polishing a back surface of the monocrystalline silicon substrate to remove a predetermined amount thereof to thereby make the monocrystalline silicon substrate thin; and a sixth step of etching the filling material in the groove in the monocrystalline silicon substrate to thereby form the beam which has the weight.

In other words, in the semiconductor mechanical sensor manufactured according to the method of present invention, the weight which is formed at the tip of the beam is excited due to static electricity which is created by applying an alternating current electric power to a side wall of the substrate which faces one surface of the weight. In such a state, in the axial direction which is perpendicular to the excitation direction of the weight, a change in the capacitance value between two electrodes arranged oppositely to each other is electrically detected so that a mechanical force which acts and changes in the same direction such as a yaw rate, an acceleration or the like is detected.

More precisely, in the semiconductor mechanical sensor according to the present invention, the weight is excited by static electricity due to alternating current electric power, and in the axial direction which is perpendicular to the direction of the excitation, a change in the capacitance value between the two electrodes arranged oppositely to each other, is electrically detected. The detected signal is superimposed on the carrier wave in the AM modulation circuit so that the carrier wave is AM modulated. Further, the signal from the AM modulation circuit is passed through the band pass filter which has a center frequency which coincides with the frequency of the carrier wave.

BRIEF DESCRIPTION OF THE DRAWINGS

FIGS. 19 to 31 are cross-sectional views each showing a configuration of an intermediate material in respective manufacturing steps.

DESCRIPTION OF THE PREFERRED EMBODIMENTS

In the following description, semiconductor mechanical sensors according to embodiments of the present invention will be described with reference to the drawings.

Figure 1:
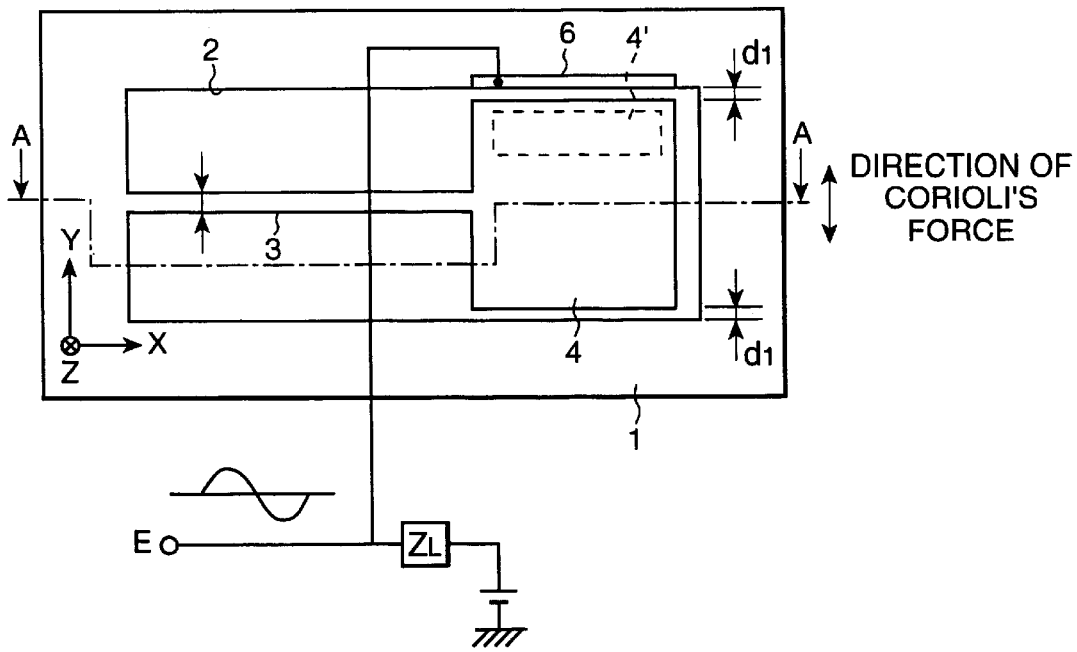
FIG. 1 is a plan view of a semiconductor mechanical sensor.
Figure 2:
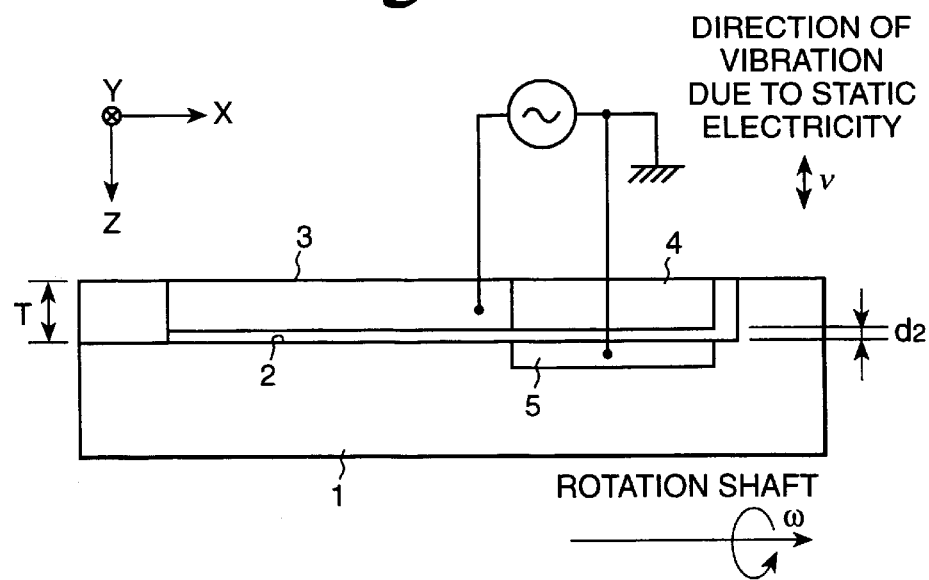
FIG. 2 is a view showing a cross section of FIG. 1 taken along the line A—A.

FIG. 1 is a plan view of a semiconductor mechanical sensor according to an embodiment of the present invention and FIG. 2 is a view showing a cross section of FIG. 1 taken along the line A—A. In the description hereinafter, to explain three dimensional directions, a right-to-left direction will be referred to as the X-axis direction, an up-down direction will be referred to as the Y-axis direction and a direction which is perpendicular to the drawing sheets will be referred to as the Z-axis direction.

FIG. 1 is a plan view showing a basic structure of a semiconductor mechanical sensor according to the present invention. The semiconductor mechanical sensor comprises: a semiconductor substrate 1; a beam 3 which is formed on the semiconductor substrate 1, the beam having a weight 4; a first pair of electrodes 5 which is formed on one surface of the weight 4 and a wall surface which corresponds to the weight surface; and a second pair of electrodes 6 which is formed on one surface of the weight 4 and a wall surface which corresponds to the weight surface in an axial direction of the weight 4 which is perpendicular to the first pair of electrodes 5.

More particularly, as clearly shown in FIGS. 1 and 2, the silicon substrate 1 is a flat plate having a rectangular shape. In the central portion of the silicon substrate 1, a rectangular recess portion 2 is formed (depth; T). Within the recess portion 2, the beam 3 which has a narrow width (width; $W_B$) extends from the left wall of the recess. At the tip of the beam 3, the weight portion 4 is formed with a width greater than the beam 3 and a square shape. The beam 3 and the weight portion 4 have the same thickness. Further, one side surface of the weight portion 4 (the top surface in FIG. 1) and the inner wall of the recess portion 2 are spaced away from each other by a small distance (distance d1). In a similar manner, the other side surface of the weight portion 4 (the bottom surface in FIG. 1) and the inner wall of the recess portion 2 are spaced away from each other by the same small distance (distance d1). Similarly, the bottom surface of the weight portion 4 and the beam 3 (the bottom surface in FIG. 2) and the bottom surface of the recess portion 2 are spaced away from each other by a small distance (distance d2).

Thus, the sensor has a cantilever structure. In this structure, the space having the distance d2 is created by etching a layer which is predeterminedly designed to be removed by a surface micro machining technique.

In addition, the beam 3 forms a wiring region for the weight portion 4 which serves as an electrode.

In the bottom surface of the recess portion 2, at a region where the recess portion 2 faces the weight portion 4, the electrode portion 5 is formed, and a portion which faces the electrode portion 5, i.e., the weight portion 4 serves as an electrode. Further, the electrode portion 6 is formed in a surface of the inner wall of the recess portion 2 facing a side of the weight portion 4 (i.e., the upper surface of the recess portion 2 in FIG. 1), and a portion facing the electrode portion 6, i.e., the weight portion 4 serves as an electrode. The electrode 5 is an electrode which provides static electricity. The electrode 6 is an electrode which detects a displacement of the weight portion 4 and forms a capacitance with the weight portion 4. In this structure, the weight portion 4 and the electrodes 5 and 6 are insulated from each other.

Figure 3:
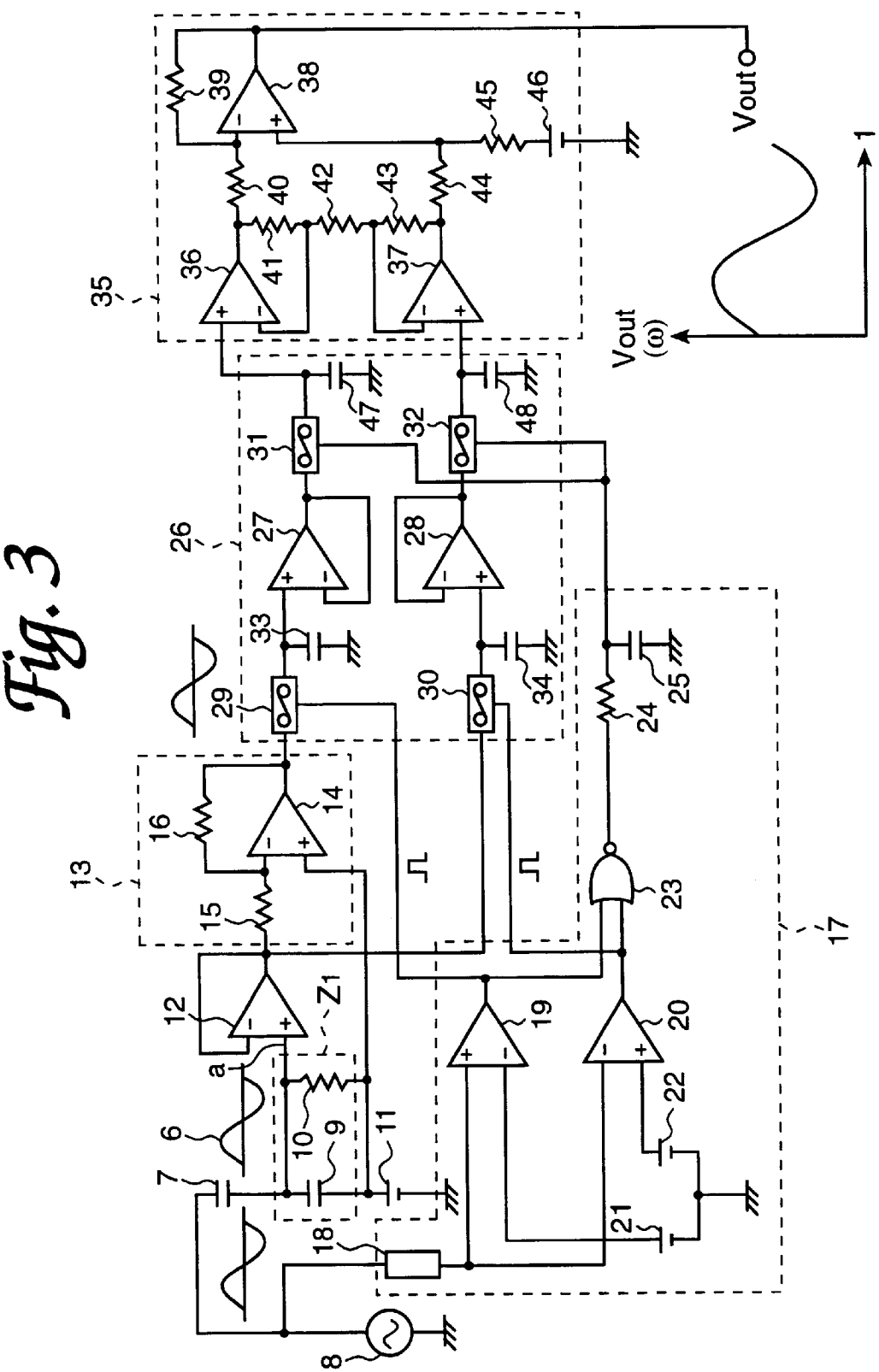
FIG. 3 is a view showing an electric circuit of a semiconductor mechanical sensor.

FIG. 3 is a view showing an electrical circuit which is used in the semiconductor mechanical sensor according to the present invention.

That is, as shown in FIG. 3, a circuit for effectively operating the semiconductor mechanical sensor according to the present invention comprises: oscillation means 8 which is connected to a capacitor portion 7 which is formed by an electrode 4' which is disposed on a side wall portion of the weight portion 4 and an electrode 6 which is disposed on a wall surface of the substrate facing the weight portion 4; impedance matching means 12 which is connected to the capacitor portion 7; inverting amplifier means 13 which is connected to the impedance matching means 12; clock signal generation means 17; and sample-and-hold means 26 which is connected to the inverting amplifier means 13 and clock signal generation means 17. In response to sample-and-hold periods which are determined based on a clock signal which is output by the clock signal generation means 17, the sample-and-hold means 26 records a peak output value of the inversion amplifier means during each sample-and-hold period and calculates a difference between the peak values in different sample-and-hold periods. Differential amplifier means 35 is provided for amplifying the difference value.

In other words, in the electrical circuit which is used in the present invention, the capacitor portion 7 is formed by the electrode 6 and the weight portion 4, and the oscillator 8 is connected to the weight portion 4 side of the capacitor portion 7. An impedance $Z_L$ is formed by a capacitor 9 and a resistor 10 connected to the electrode 6 side of the capacitor portion 7. A power source 11 is connected to the capacitor 9.

Figure 4:
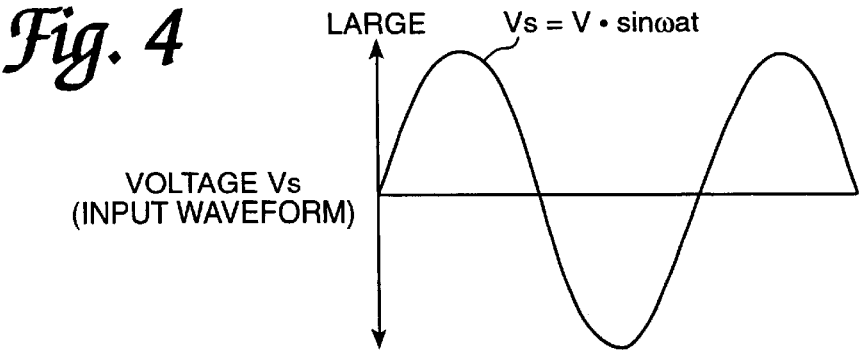
FIG. 4 is a view showing the waveform of an input signal.
Figure 5:
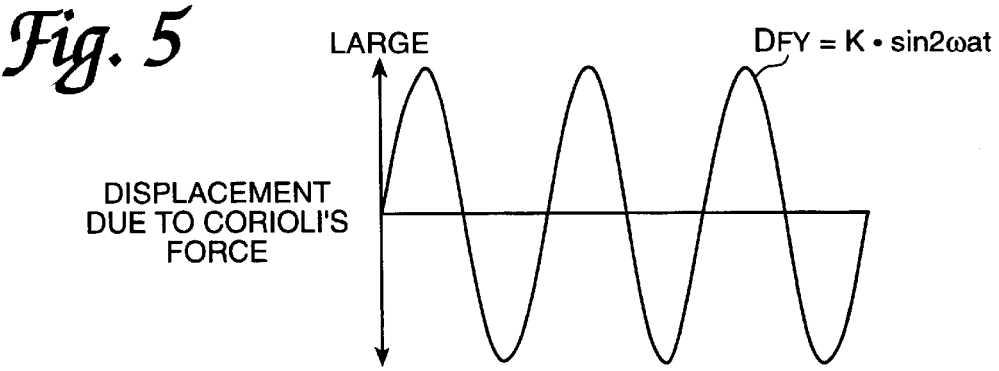
FIG. 5 is a view showing a quantity of displacement.
Figure 6:
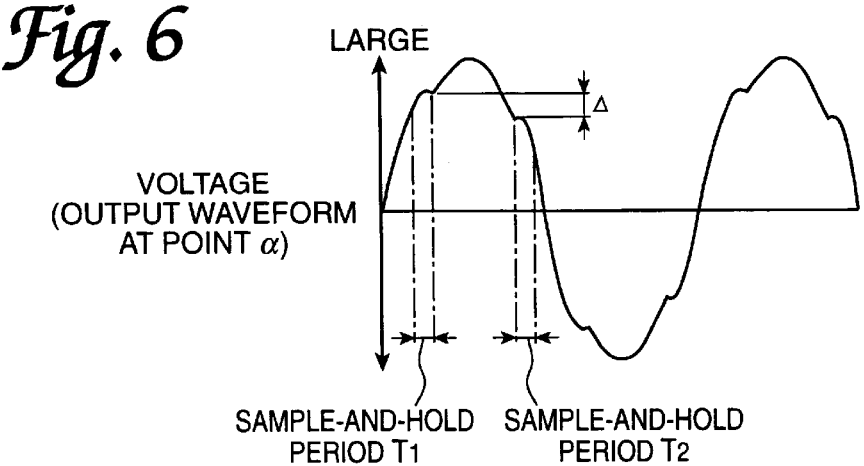
FIG. 6 is a view showing a signal waveform.

To one end of the impedance $Z_L$, the impedance matching means 12, comprising an operational amplifier, is connected at a point α which is created by a change in the capacitance value of the capacitor portion 7. Here, an alternating current voltage source $V_S$ (=V·sin$\omega_S$t) shown in FIG. 4 is applied between the electrode 5 and the weight portion (electrode) 4 of FIG. 2. In such a state, when the weight portion 4 is displaced by Coriolis deflection as shown in FIG. 5, a waveform as shown in FIG. 6 appears at a non-inverted input terminal of the impedance matching means 12 (the point α in FIG. 3).

The output of the impedance matching means 12 of FIG. 3 is coupled to the inverting amplifier circuit 13. The inverting amplifier means 13 is formed by an operational amplifier 14 and resistors 15 and 16. A signal from the impedance matching means 12 is inverted and amplified by the inverting amplifier means 13.

The clock signal generation means 17 is comprised of a voltage adjustor 18, two comparators 19 and 20, power sources 21 and 22, a NOR gate 23, a resistor 24 and a capacitor 25. In the clock signal generation means 17, sample-and-hold periods T1 and T2 shown in FIG. 6 are generated.

The sample-and-hold circuit 26 is formed by two operational amplifiers 27 and 28, switches 29, 30, 31 and 32 and capacitors 33, 34, 47 and 48. In the sample-and-hold periods T1 and T2 shown in FIG. 6 generated by the clock signal generation means 17, the switches 29, 30, 31 and 32 are opened and closed, whereby a sample-and-hold operation is performed during these periods.

The differential amplifier circuit 35 is formed by operational amplifiers 36, 37 and 38, resistors 39, 40, 41, 42, 43, 44 and 45 and a power source 46. From an output value available from the sample-and-hold circuit 26, a difference between peak values during the sample-and-hold periods T1 and T2 is calculated (i.e., Δ in FIG. 6) and amplified.

At the output terminal of the operational amplifier 38, a sensor output $V_{out}$ is obtained.

Next, functions of a semiconductor mechanical sensor having a construction as explained above will be described with reference to FIG. 12.

Figure 12:
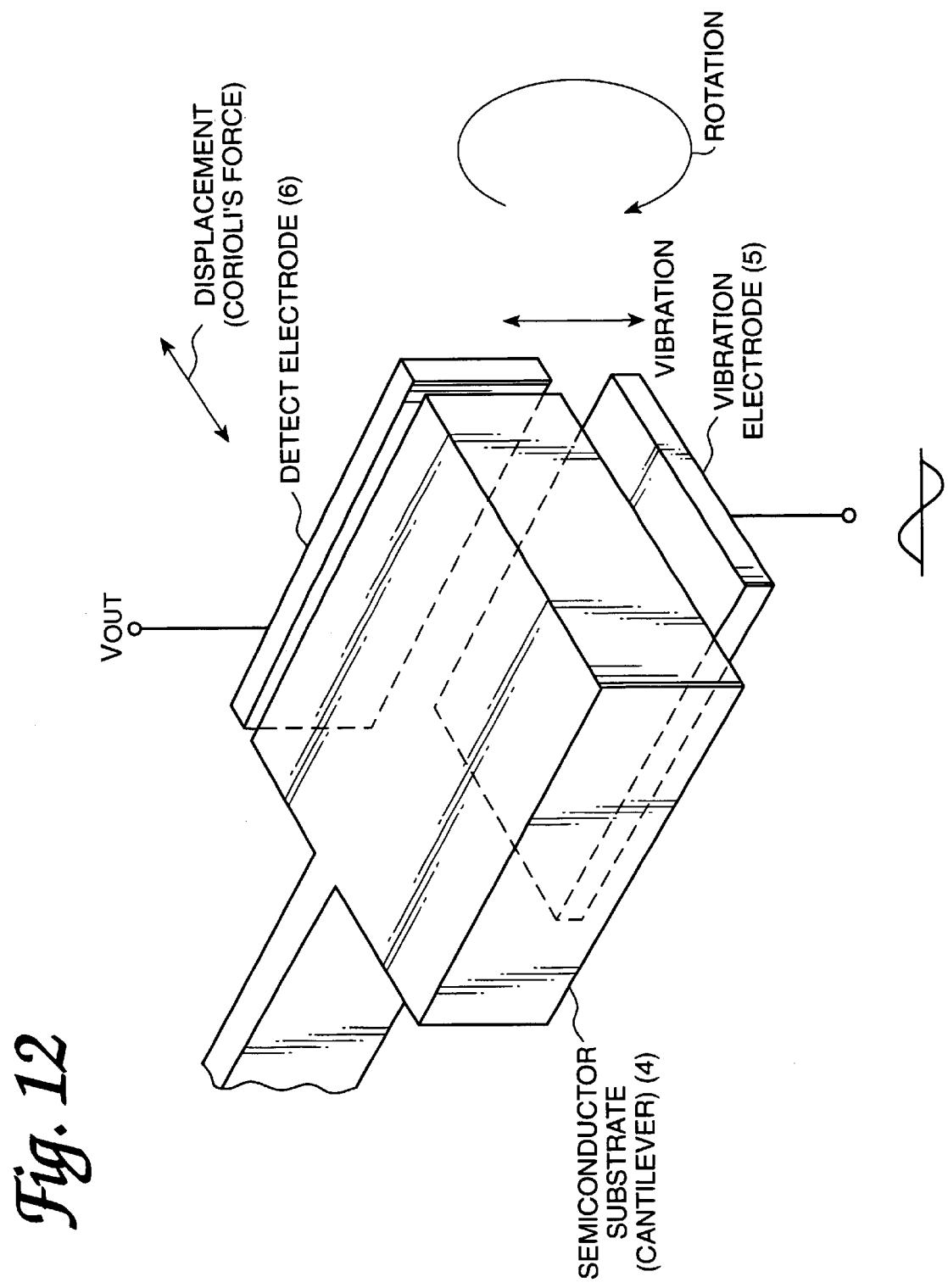
FIG. 12 is an explanatory diagram showing the principles of the present invention.

As shown in FIG. 12, in the present invention, the beam structure 3 is formed in a portion of the semiconductor substrate 1 spaced away from the semiconductor substrate 1, and an alternating current electric power is applied to a wall surface of the substrate which faces one surface of the weight 4 which is formed at the tip of the beam 3, so as to generate static electricity and excite the weight. In the axial direction which is perpendicular to the direction of the excitation of the weight, the electrodes are disposed in a facing relation with each other on the wall surfaces of the substrate which face the one surface of the weight and the surface of the beam. A change in the capacitance value between the facing electrodes is electrically detected so that a mechanical forces which act thereto in the same direction is detected.

Between the electrode 5 and the weight portion (electrode) 4 of FIG. 12, an alternating current voltage $V_S$ (=V·sin$\omega_S$t) is applied where $\omega_S$ is a rotational angular velocity. As a result, static electric power $F_E$ as defined by Equation 1 below is created.

$$F_E = \epsilon_0 \cdot S \cdot V_S^2 / 2d^2 \tag{1}$$

In the direction Z, a displacement as defined by Equation 2 below is generated.

$$D_Z = \frac{F_E \cdot L^3}{3 \cdot E \cdot I_Z} + \frac{F_E \cdot L^2 \cdot L_m}{2 \cdot E \cdot I_Z} \tag{2}$$

where $\epsilon_0$ is a dielectric constant, S is a facing area of the electrodes, d is a distance between the electrodes, L is the length of the beam, $L_m$ is the length of the weight portion 4, $I_Z$ is a secondary moment of area of the beam 3 in the Z-axis direction, and E is a Young's modulus.

Differentiating Equation 2 by time t, the velocity $V_Z$ vibrates as:

$$V_Z = dD_Z/dt \tag{3}$$

At this stage, with a rotational angular velocity ω applied to the axis X which is perpendicular to the axis Z, the Coriolis effect Fc defined by $$Fc = 2mV_Z\omega \tag{4}$$

is created in the axis-Y direction.

In Equation 4, m is the mass of the weight portion 4.

Due to the Coriolis effect Fc, a displacement $D_Y$ which is expressed by Equation 5 below is generated in the Y-axis direction.

$$D_Y = \frac{F_C \cdot L^3}{3 \cdot E \cdot IY} + \frac{F_C \cdot L^2 \cdot L_m}{2 \cdot E \cdot IY} \tag{5}$$

where IY is a secondary moment of area in the axis-Z direction. Hence, a capacitance between the electrodes $C_Y$ is expressed by Equation 6 below.

$$C_Y = \varepsilon_0 \frac{S_y}{dy + DY} \tag{6}$$

where $S_y$ is the faced area of the electrodes and $d_y$ is the distance between the electrodes.

Due to a change in the value $C_y$, a voltage Vω defined by Equation 7 is created at the output terminal (output voltage) $V_{out}$.

$$V\omega = \frac{Z}{Z + 1/\omega_s C_y} \cdot V_S \tag{7}$$

In other words, the output Vω changes in accordance with the rotational angular velocity ω and the angular velocity ω is calculated as the change in the value Vω.

Next, a description will be given of how the signal is processed in the circuit with reference to FIG. 3.

The input waveform applied to the weight portion 4 is a sinusoidal wave as shown in FIG. 4. Because of the Coriolis effect, the weight portion 4 is displaced in accordance with a sinusoidal wave which has a frequency double that of the input signal as can be seen from Eq. 5 and FIG. 5. This creates a waveform at the non-inverted input terminal α of the impedance matching means 12 of FIG. 3, as shown in FIG. 6.

The most largely deformed portions of the input waveform of the capacitor portion 7 during the sample-and-hold periods T1 and T2 shown in FIG. 6, i.e., the portions corresponding to the peak displacement of the weight portion 4 are peak-held by the operational amplifiers 27 and 28, and the resultant difference is amplified by the operational amplifiers 36 and 37, whereby the voltage output $V_{out}$ which corresponds to the angular velocity ω is calculated.

Figure 7:
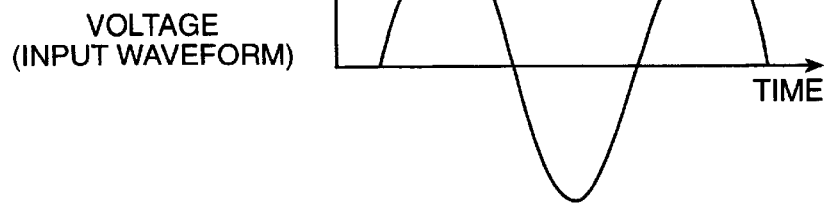
FIG. 7 is a view showing a signal waveform.
Figure 8:
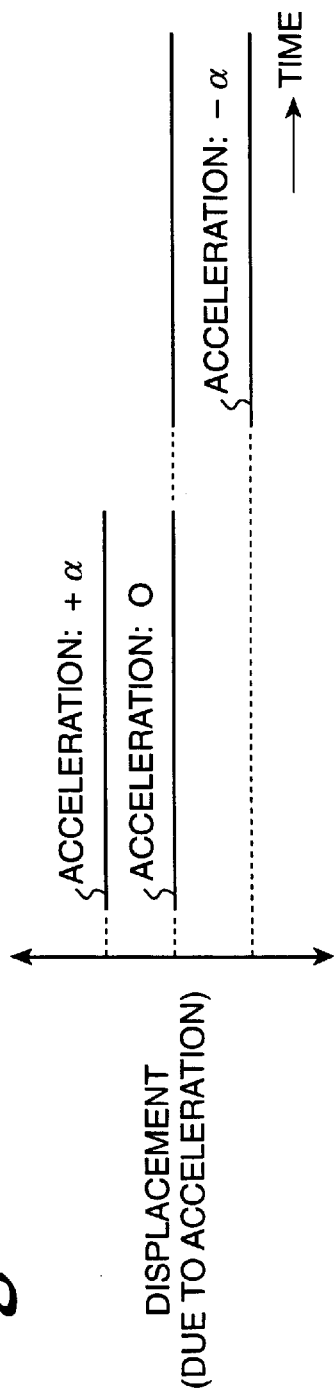
FIG. 8 is a view showing a quantity of displacement.
Figure 9:
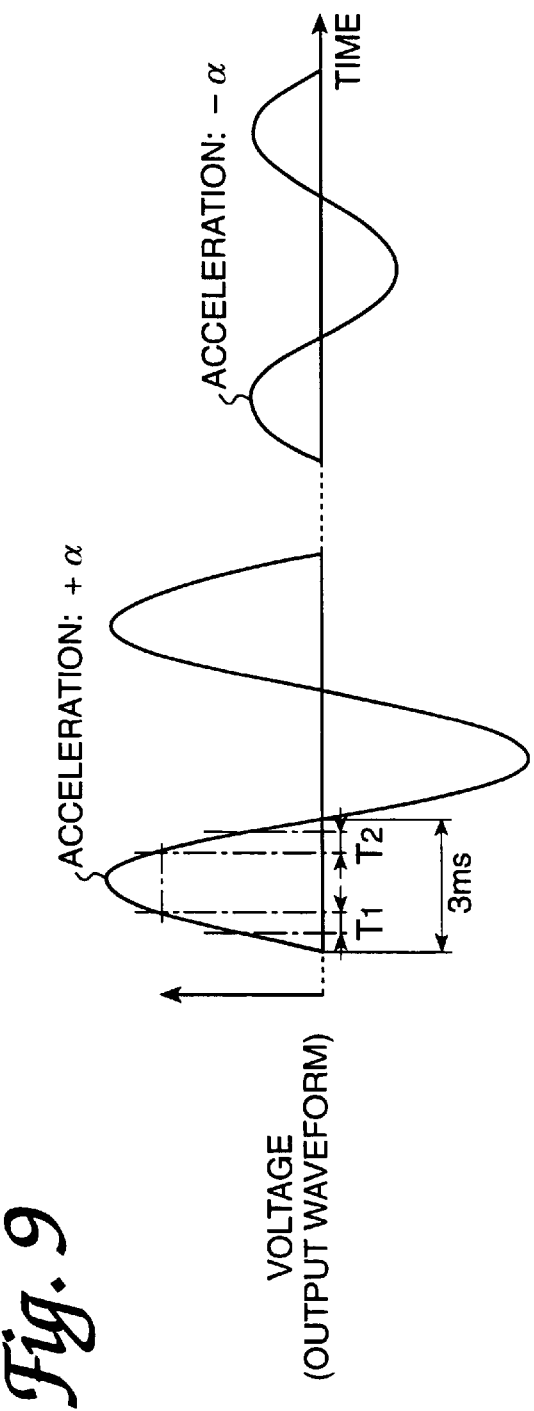
FIG. 9 is a view showing a signal waveform.

Next, we assume that an acceleration of a frequency fa (in the direction Y) is applied as a disturbance noise. Here, if the relation $$fa \ll 2\pi\omega_S \qquad (8)$$

holds, with respect to the input waveform shown in FIG. 7, the acceleration is regarded as a displacement only on one side as shown in FIG. 8, and therefore, the output waveform shown in FIG. 9 does not include a deformed portion.

In the processing in the circuit shown in FIG. 3, this waveform is cancelled. For instance, where the characteristic frequency of the cantilever 3 is 4 KHz and $\omega_S/2\pi$=3 KHz, since the frequency component of acceleration of an automobile is around 300 Hz at maximum, Eq. 8 holds.

Further, since the frequency component is even smaller for displacement due to temperature, Eq. 8 holds satisfactorily.

In this manner, in a sensing operation, the processing circuit cancels most noises interfering with detection or the angular velocity. Hence, the angular velocity is detected accurately.

In addition, in the electrical circuit as above according to the present invention, since a deformed waveform of the beam due to acceleration and a deformed waveform of the beam due to a yaw rate are different from each other and clearly distinguishable from each other, the semiconductor mechanical sensor according to the present invention can be used as both an acceleration sensor and a yaw rate sensor, as well as for other sensors.

As described above, in the above example of the present invention, the beam structure is formed in a portion of the silicon substrate 1 (semiconductor substrate) spaced away from the silicon substrate 1, and an alternating current electric power is applied to a wall surface of the substrate which faces one surface of the weight which is formed at the tip of the beam, so as to deflect the weight by static electricity. In the axial direction perpendicular to the direction of the excitation of the weight, the electrodes 6 are disposed in a facing relation on the wall surfaces of the substrate facing the one surface of the weight and the surface of the beam. A change in the capacitance value between the facing electrodes is electrically detected so that mechanical forces which act in the same direction, i.e., an acceleration or a yaw rate, is detected. Thus, the semiconductor mechanical sensor has a new structure.

Figure 10:
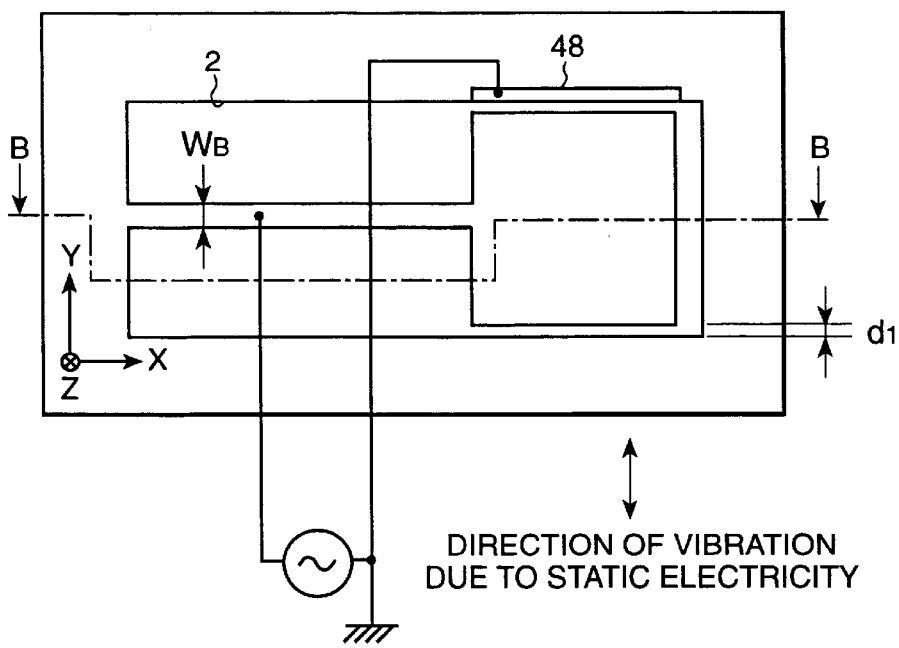
FIG. 10 is a plan view of a semiconductor mechanical sensor according to another embodiment.
Figure 11:
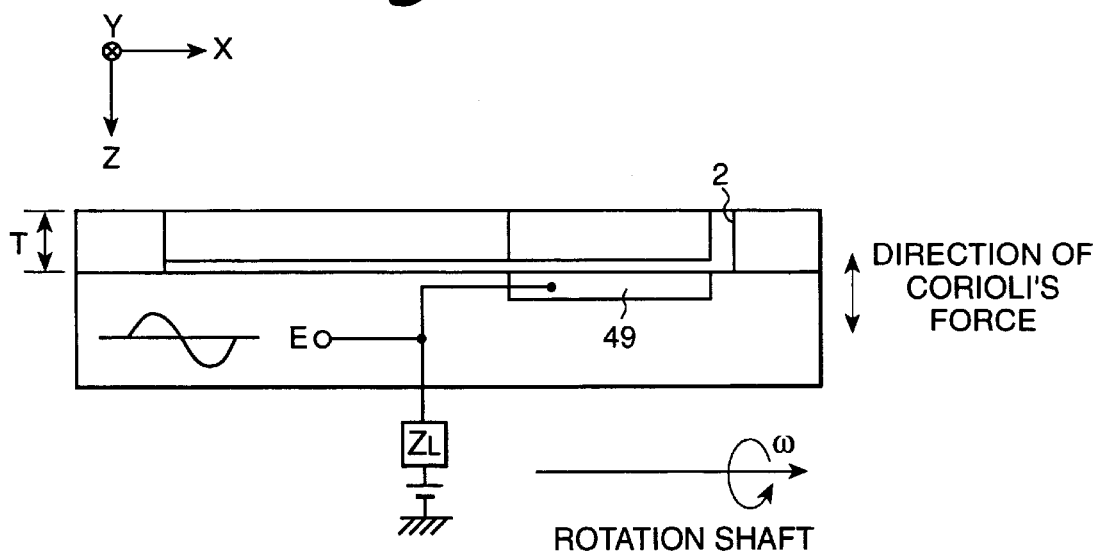
FIG. 11 is a view showing a cross section of FIG. 10 taken along the line B—B.

The present invention is not limited to the example above. For example, as shown in FIGS. 10 and 11, as a portion to which static electricity is to be applied, an excitation electrode 48 may be disposed in one side wall of the recess portion 2, and a detect electrode 49 may be disposed on the bottom surface of the recess portion 2.

As hereinabove described in detail, the present invention provides a semiconductor mechanical sensor which has a new structure.

Incidentally, the semiconductor mechanical sensor structure as above has an inconvenience that in amplifying a signal of the sensing part, noise (e.g., thermal noise, 1/f noise) is also amplified, which makes it difficult to improve the S/N ratio.

As a result of study devoted to solving this problem, the inventor of the present invention has come to the conclusion that the problem can be solved if the semiconductor mechanical sensor described above further comprises an AM modulation circuit for superimposing a signal from the physical force detecting electrode onto a carrier wave, and a band pass filter for passing a signal from the AM modulation circuit whose center frequency coincides with the carrier wave.

Figure 13:
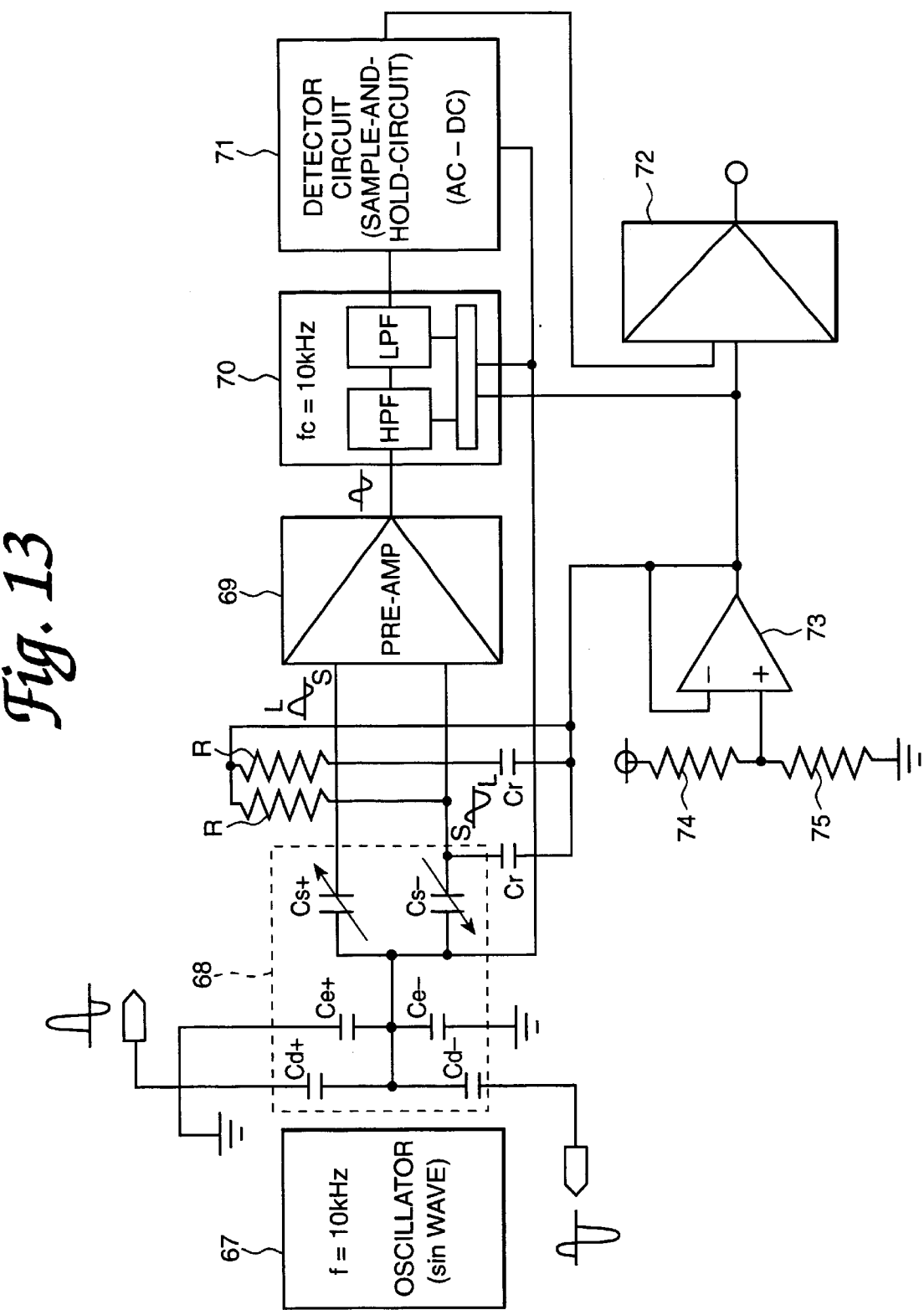
FIG. 13 is a view showing an electric circuit of a semiconductor mechanical sensor.
Figure 14:
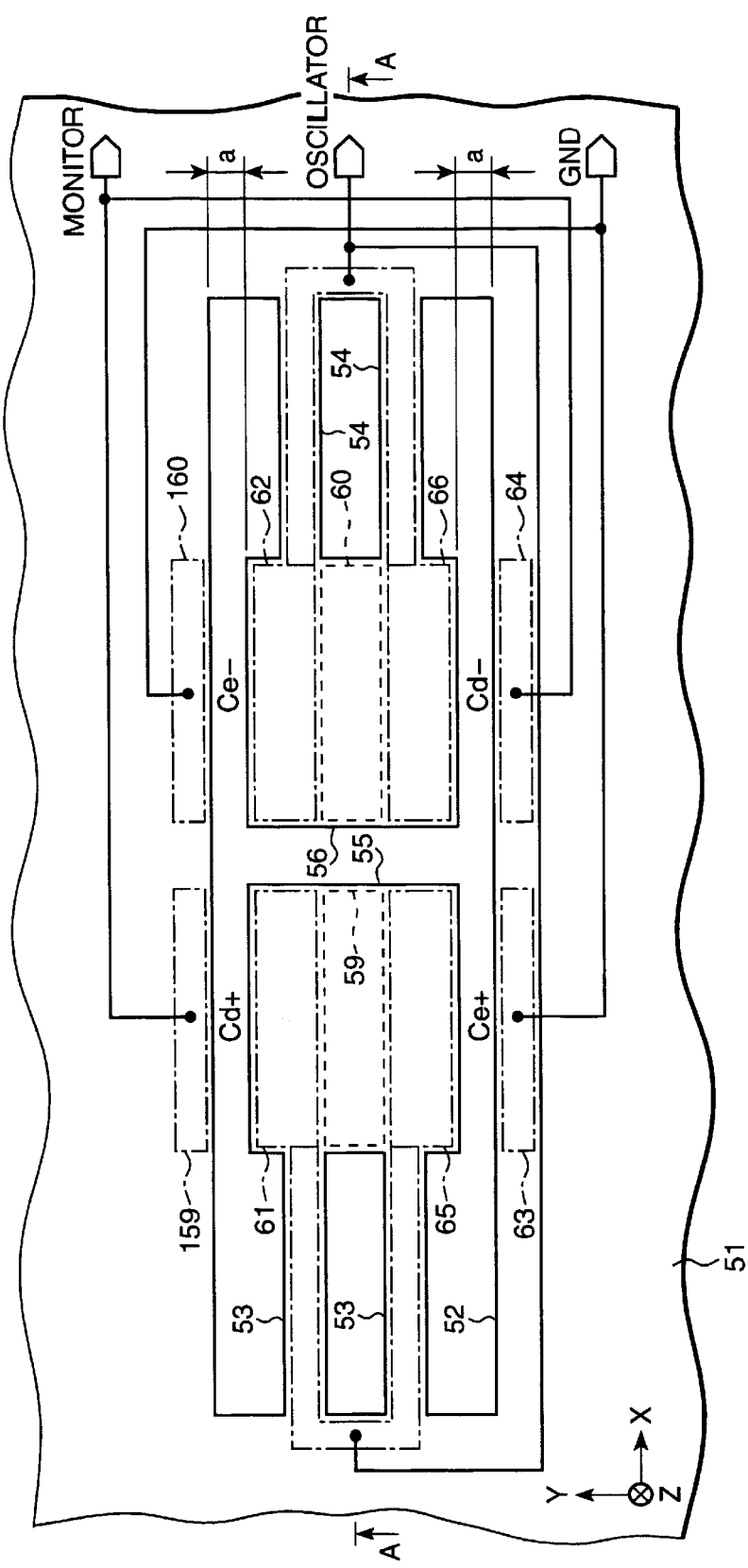
FIG. 14 is a plan view of a semiconductor mechanical sensor.
Figure 15:
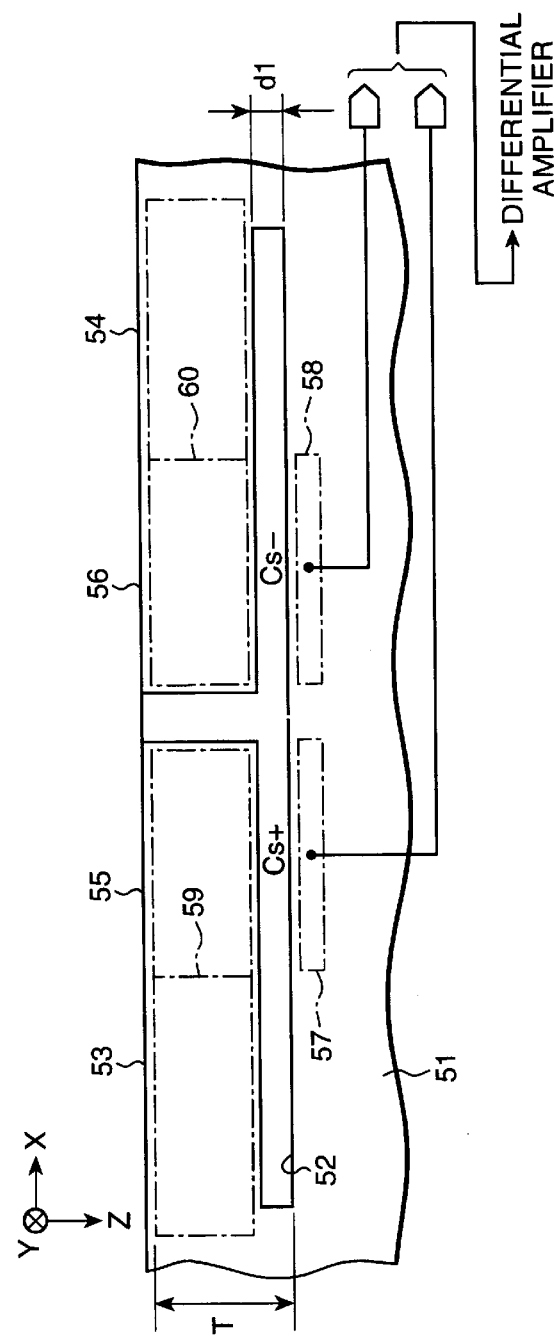
FIG. 15 is a view showing a cross section of FIG. 14 taken along the line A—A.

In the following, an embodiment of a circuit structure of the example above according to the present invention will be described with reference to the drawings. FIG. 13 is a plan view of an electrical circuit according to the present invention, FIG. 14 is a plan view showing a semiconductor mechanical sensor, and FIG. 15 is a view showing a cross section of FIG. 14 taken along the line A—A. In the description below, to explain three dimensional directions, a right-to-left direction will be referred to as the X-axis direction, an up-down direction will be referred to as the Y-axis direction and a direction which is perpendicular to the drawing sheets will be referred to as the Z-axis direction.

FIG. 14 shows an example where a semiconductor mechanical sensor device comprises two semiconductor mechanical sensors according to the present invention disposed as a pair. In such a structure, a change in a certain physical force and a change in a different physical force can be separately detected and detection of a change in the physical force can be achieved accurately, for instance.

In FIG. 14, a silicon substrate 51 is a flat plate and includes a rectangular recess portion 52 (depth; T). Within the recess portion 52, two beams 53 extend from the left side of FIG. 14. At the tips of the beams 53, a weight 55 is formed. On the other hand, within the recess portion 52, two beams 54 extend from the right side of FIG. 14, and at the tips of the beams 54, a weight 56 is formed. The weights 55 and 56 are wider than the beams 53 and 54 and each is shaped in a rectangular shape. The beams 53 and 54 and the weights 55 and 56 have the same thickness.

In addition, one side surface of the weight 55 (the top surface in FIG. 14) and the inner wall of the recess portion 52 are spaced away from each other by a small distance (distance a). In a similar manner, the other side surface of the weight 55 (the bottom surface in FIG. 14) and the inner wall of the recess portion 52 are spaced away from each other by the same small distance a. Similarly, the bottom surface of the weight 55 (the bottom surface in FIG. 15) and the bottom surface of the recess portion 52 are spaced away from each other by a small distance (distance d1).

On the other hand, one side surface of the weight 56 (the top surface in FIG. 14) and the inner wall of the recess portion 52 are spaced away from each other by the same small distance. In a similar manner, the other side surface of the weight 56 (the bottom surface in FIG. 14) and the inner wall of the recess portion 52 are spaced away from each other by the same small distance a. Similarly, the bottom surface of the weight 56 (the bottom surface in FIG. 15) and the bottom surface of the recess portion 52 are spaced away from each other by the small distance d1.

Thus, the illustrated sensor has a cantilever structure. In this structure, the distance d1 is created by etching a layer which is predeterminedly designed to be removed, by a surface micro machining technique.

In FIG. 15, in the bottom surface of the recess portion 52 where the recess portion 52 faces the weights 55 and 56, electrodes 57 and 58 are formed. In portions of the weights 55 and 56 where they face the electrodes 57 and 58, electrodes 59 and 60 are formed. Further, in an inner wall surface of the recess portion 52 where the recess portion 52 faces the weights 55 and 56 (i.e., in the upper surface of the recess portion 52 in FIG. 14), electrodes 159 and 160 are formed, and in portions of the weights 55 and 56 where they face the electrodes 159 and 160, electrodes 61 and 62 are formed.

In an inner wall surface of the recess portion 52 where the recess portion 52 faces the weights 55 and 56 (i.e., in the lower surface of the recess portion 52 in FIG. 14), electrodes 63 and 64 are formed, and in portions of the weights 55 and 56 where they face the electrodes 63 and 64, electrodes 65 and 66 are formed.

In addition, in this structure, the electrodes 57, 58, 59, 60, 61, 62, 63, 64, 159 and 160 are insulated from each other.

A capacitor $C_{s+}$ is created by the electrodes 59 and 57, a capacitor $C_{s-}$ is created by the electrodes 60 and 58, a capacitor $C_{d+}$ is created by the electrodes 159 and 61, a capacitor $C_{d-}$ is created by the electrodes 64 and 66, a capacitor $C_{e+}$ is created by the electrodes 65 and 63, and a capacitor $C_{e-}$ is created by the electrodes 160 and 62.

The beams 53 and 54 form wiring regions for the electrodes 59 (61, 65) and 60 (62, 66), respectively.

For clarity of explanation, although the electrodes 59, 61 and 65 are described as different electrodes, they are one and the same electrode (same potential). Likewise, although described as different electrodes for clarity of explanation, the electrodes 60, 62 and 66 are one and the same electrodes (same potential).

FIG. 13 shows an electrical circuit of the semiconductor mechanical sensor according to the present invention.

The processing circuit of the sensor comprises an oscillator 67, a sensing part 68, a differential amplifier 69, a band pass filter 70, a sample-and-hold circuit 71 and a subsequent stage amplifier 72.

A capacitor Cr of FIG. 13 is not shown in FIGS. 14 and 15. However, the capacitor Cr is connected in parallel with a resistor R and has a fixed capacitance value $Cr=C_{s+}=C_{s-}$.

The capacitors $C_{e+}$ and $C_{e-}$ drive the weights 55 and 56 by static electric force Fe. The capacitors $C_{s+}$ and $C_{s-}$ are capacitors for detecting the amount of displacement of the weights 55 and 56 in the Z-axis direction due to the Coriolis effect Fc.

The capacitors $C_{d+}$ and $C_{d-}$ shown in FIG. 14 are monitor capacitors for detecting the amount of movement of the weights 55 and 56 in the Y-axis direction due to the drive capacitors $C_{e+}$ and $C_{e-}$.

Next, the structure shown in FIG. 13, except for the sensing part 68, will be described.

The oscillator 67 has an oscillation frequency of 10 KHz and provides a voltage (alternating current electric power) for driving the weights 55 and 56 and a signal (carrier wave) to the capacitors $C_{s+}$ and $C_{s-}$. The resistor R applies a bias voltage to any one of connection portions between the capacitors $C_{s-}$ or $C_{s+}$ and Crs, and has a resistance $R \gg 1/\omega Cr$. By applying a bias, each one of the resistors R makes subsequent signal processing possible.

The differential amplifier 69 amplifies a difference voltage between inputs (capacitors $C_{s+}$ and $C_{s-}$). The band pass filter 70 has a center frequency of 10 KHz which coincides with the frequency of the carrier wave. In addition, the band pass filter 70 attenuates signals other than those having a predetermined frequency band (near the center frequency). In this example, the band pass filter 70 is formed by a switched-capacitor filter (S.C.F.).

The sample-and-hold circuit 71 (detector circuit) demodulates a signal which is AM modulated as will be described later. An operational amplifier 73 and resistors 74 and 75 form a reference voltage for use within the processing circuit. The subsequent stage amplifier 72 amplifies a detected signal. The subsequent stage amplifier 72 may be omitted.

In this example, the electrodes 57, 58, 59 and 60 form a yaw rate detecting electrode while the oscillator 67 and the differential amplifier 69 form an AM modulation circuit.

Next, the functions of a semiconductor mechanical sensor having the construction described above will be described.

When the oscillator 67 applies a voltage $V_{IN}$ (=$V_{CM} \cdot \cos\omega_c t$) to the capacitors $C_{e-}$ and $C_{e+}$, static electric force Fe as defined by Equation 9 below is created.

$$Fe=(\epsilon_0 S/2a^2) \cdot V_{IN}^2 \qquad (9)$$

where $\epsilon_0$; a dielectric constant a; a distance between the capacitors $C_{e-}$ and $C_{e+}$ S; a faced electrode area of the capacitors $C_{e-}$ and $C_{e+}$ Due to the static electric force Fe, the weights 55 and 56 are displaced in the Y-axis direction. Assuming that the amounts of the displacements are Dy, the relationship shown in Equation 10 is created.

$$Dy=KFe \qquad (10)$$

where K: a constant which is determined by the cantilever. Here, it is to be noted that the weights 55 and 56 move in different directions.

From Eqs. 9 and 10, where the velocities in the Y-axis direction of the weights 55 and 56 are $V_{y55}$ and $V_{y56}$, respectively, the following equation (11) is obtained.

$$V_{y55} = -V_{y56} \qquad (11)$$
$$= K \cdot (\epsilon_0 S/4a^2) \cdot V_{CM}^2 \cdot 2\omega_c \cdot \sin 2\omega_c^t$$

At this stage, if the axis X is the rotation axis, and when the weight is rotated with respect to the axis X rotates at the angular velocity $\omega$, Coriolis effect $F_{c55}=2mV_{y55}\omega$, $F_{c56}=2mV_{y56}\omega$ are created at the axis z.

As a result, the weights 55 and 56 are displaced in the Z-axis direction. Assuming that the displacements are $D_{z55}$ and $D_{z56}$, $$D_{z55}=L_{55} \cdot F_{c55}$$
$$D_{z56}=L_{56} \cdot F_{c56} \qquad (12)$$

where $L_{55}$, $L_{56}$ are constants which are determined by the cantilever.

If the weights 55 and 56 and the cantilever are formed to have the same dimensions, $L_{55}=L_{56}$, and hence, $|D_{z55}|=|D_{z56}|=\Delta d$.

In other words, the capacitance values of $C_{s+}$ and $C_{s-}$ are $$C_{s+}=(\epsilon_0 \cdot S)/(d+\Delta d)$$
$$C_{s-}=(\epsilon_0 \cdot S)/(d-\Delta d) \qquad (13)$$

Hence, an output $V_{pre}$ of the differential amplifier 69 is $$V_{pre} = V_{IN} \cdot \{C_{S+}/(C_{S+}+Cr) - C_{S-}/(C_{S-}+Cr)\} \cdot AV1 \qquad (14)$$
$$\approx V_{IN} \cdot (-\Delta d/2d) \cdot AV1$$

where VA1 is an amplification factor of the differential amplifier 67.

From Eqs. 11 and 12, $\Delta d$ is $$\Delta d=L_{55} \cdot 2m \cdot K(\epsilon_0 \cdot S/4a^2) \cdot V_{CM}^2 \cdot 2\omega_c \cdot \omega \cdot \sin 2\omega_c t \qquad (15)$$

On the other hand, from Eqs. 14 and 15, $$V_{pre}=AV1 \cdot V_{CM}^3 \cdot L_{55} \cdot 2m \cdot K(\epsilon_0 \cdot S/4a^2) \cdot \omega_c \cdot \omega \cdot (\sin\omega_c t+\sin 3\omega_c t) \qquad (16)$$

In Eq. 16, $VCM3 \cdot L_{55} \cdot 2m \cdot K(\epsilon 0 \cdot S/4a2) \cdot \omega_c$ on the right side is a constant which is determined by the structure of the cantilever and a condition of the input voltage. From Eq. 16, it is understood that the value $V_{pre}$ indicates a voltage which is in proportion to the angular velocity $\omega$ which is to be detected. The value $V_{pre}$ is expressed as a voltage output which is AM modulated to the frequency of the input signal $f_{IN}=\omega_c/2\pi$ and a frequency which is triple the same.

The foregoing has referred to a detected signal alone. However, noise may be generated by circuit elements of the differential amplifier 69 when a signal is processed in the differential amplifier 69, and noise may be introduced into the power source system from outside. These noises are also amplified by the differential amplifier 69. Hence, from Eq. 16, $$V_{pre}=AV1 \cdot V_{CM}^3 \cdot L_{SS} \cdot 2m \cdot K(\epsilon_0 \cdot S/4a^2) \cdot \omega_c \cdot \omega \cdot (\sin\omega_c t + \sin 3\omega_c t) + AV1 \cdot V_N \quad (17)$$

Thus, $AV1 \cdot V_N$ is created which expresses a noise which degrades the S/N ratio of the angular velocity $\omega$ to be detected.

To deal with this, as shown in Eq. 17, signal data concerning the angular velocity to be detected, is AM modulated by a certain modulator and passed through the band pass filter 70, having a center frequency $f_c=\omega_c 2\pi$, whereby the S/N ratio is improved.

Assume that an output of the band pass filter 70 having $5_c=\omega_c/2\pi$ is $V_{BPF}$, $$V_{BPF}=AV1 \cdot V_{CM}^3 \cdot L_{SS} \cdot 2m \cdot K(\epsilon_0 \cdot S/4a^2) \cdot \omega_c \cdot \omega \cdot \sin\omega_c t + AV1 \cdot V_N(f_c) \quad (18)$$

The value $V_{BPF}$ is expressed as shown in Eq. 18, and therefore, only $AV1 \cdot V_N(f_c)$, i.e., an noise component whose frequency component is equal to $f_c$ is left. Hence, $$AV1 \cdot V_N >> AV1 \cdot V_N(f_c) \quad (19)$$

Thus, an output which is in proportion to the angular velocity $\omega$ and which has a high S/N ratio is obtained. By processing this output in the sample-and-hold circuit 71 (detector circuit) if necessary, an output $V_{out}$ which is in proportion to the angular velocity $\omega$ is obtained as below.

$$V_{out} \approx AV1 \cdot V_{CM}^3 \cdot L_{SS} \cdot 2m \cdot K(\epsilon_0 \cdot S/4a^2) \cdot \omega_c \cdot \omega \quad (20)$$

This output is amplified, if necessary, in the subsequent stage amplifier 72.

As described above, in the present embodiment, the oscillator 67 and the differential amplifier 69 (AM modulation circuit) superimpose signals from the electrodes 57, 59 and 58, 60 (yaw rate detect electrodes) on a carrier wave, and a signal from the differential amplifier 69 is passed through the band pass filter 70 which has a center frequency which coincides with that of the carrier wave. Hence, in processing a signal by the differential amplifier 69, even if noise is generated in a circuit element of the differential amplifier 69 when a signal is processed in the differential amplifier 69 and other noise is introduced into the power source system from outside, these noises are removed. That is, noise (e.g., a thermal noises, a 1/f noise) is deenphasized and therefore the S/N ratio is improved.

As described above, the present embodiment provides an improved S/N ratio.

However, with respect to a semiconductor mechanical sensor such as the semiconductor yaw rate sensor above which is movable in two directions, the example described above is insufficient in terms of structure. To manufacture the sensor, an efficient manufacturing method for a high productivity has not been proposed yet.

To deal with this, in addition to the examples described above, the present invention offers a semiconductor mechanical sensor which has an optimum structure and methods of efficiently manufacturing the semiconductor mechanical sensors according to the examples described above. That is, according to an other example of the present invention, a semiconductor mechanical sensor comprises: a thin monocrystalline silicon substrate which is joined onto a substrate through an insulation film; a beam which is formed in the monocrystalline silicon substrate and which has a weight; a first electrode which is formed in one surface of said weight and a wall surface which corresponds to said weight surface; and a second electrode which is formed in one surface of the weight and a wall surface which corresponds to the weight surface in an axial direction of the weight which is perpendicular to the electrode, and either one of the electrodes is preferably formed on the major surface of the monocrystalline silicon substrate in parallel with the monocrystalline silicon substrate.

Further, all electrode contacting portions are preferably formed on the same surface of the thin monocrystalline silicon substrate.

Describing the semiconductor mechanical sensor according to the present invention in more detail, the semiconductor mechanical sensor has a structure in which a plurality of groove portions 201 are formed in the tip portion 139 of a weight portion 139, an electrode is disposed on an inner wall portion of each of groove portions 201, and a fixed member 202 extends in each groove portion 201 and an other electrode is disposed on a side surface portion which faces the inner wall portion of the groove portion of the weight portion 4 of the fixed member 202.

In this example, a first electrode and a second electrode which is disposed in an axial direction perpendicular to the first electrode detect a mechanical quantity which is applied to a beam having a weight.

Now, a semiconductor mechanical sensor having such a structure according to the present invention will be described with reference to FIGS. 16 to 18.

Figure 17:
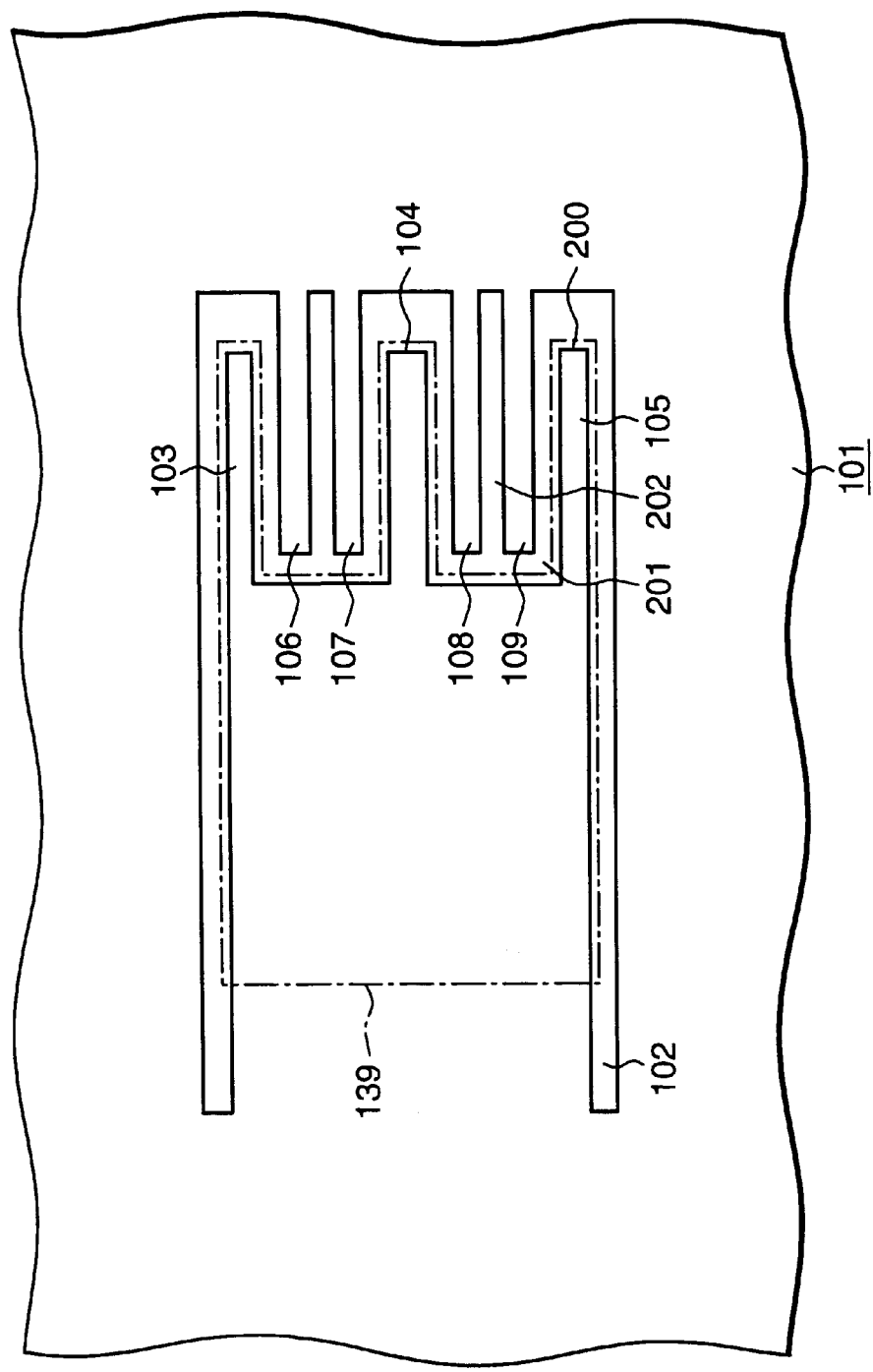
FIG. 17 is a schematic plan view of the semiconductor mechanical sensor according to the embodiment shown in FIG. 16.

FIG. 17 is a schematic plan view of the semiconductor mechanical sensor according to the present example. That is, in the illustrated sensor, a cantilever 102 is formed in a monocrystalline silicon substrate 101 so as to include a weight 139 at the tip. In a tip portion 200 of the weight 139, three projections 103, 104 and 105 are formed spaced from each other to extend along the elongation of the beam, and a groove portion 201 is formed between the three projections 103, 104 and 105. On the monocrystalline silicon substrate 101 side facing the tip portion surface 200 of the cantilever 102 (weight 139), between the projections 103 and 104, two projections 106 and 107 are formed spaced from each other to extend in parallel with the projections 103 and 104, thereby forming a fixed portion 202. In a similar manner, on the monocrystalline silicon substrate 101 side facing the tip portion surface of the cantilever 102 (weight 139), between the projections 104 and 105, two projections 108 and 109 are formed spaced from each other to extend parallel to the projections 104 and 105.

Figure 18:
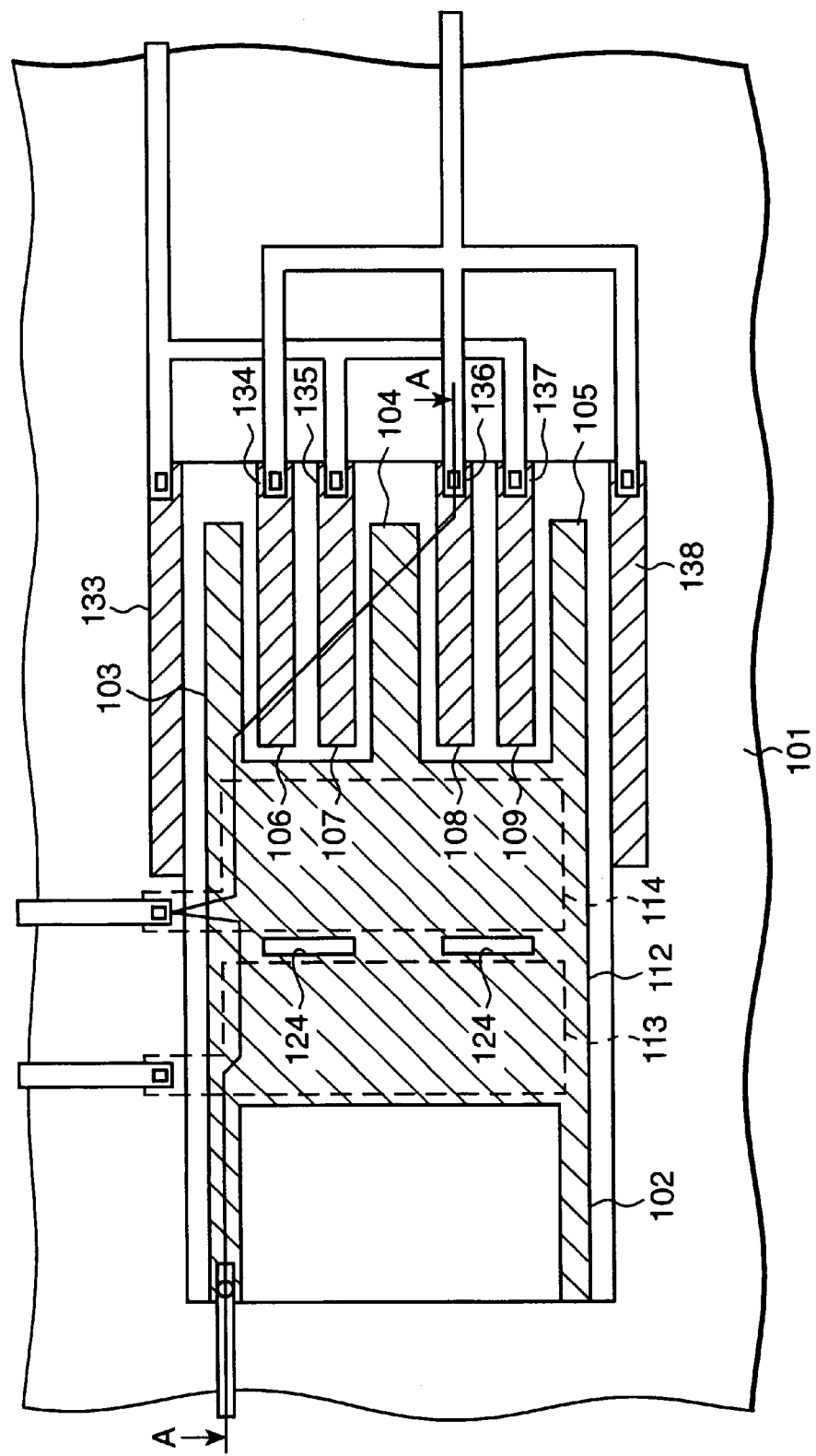
FIG. 18 is a plan view of the semiconductor mechanical sensor according to the embodiment shown in FIG. 16.

FIG. 18 is a plan view showing the semiconductor mechanical sensor including the electrodes. FIG. 16 is a view showing a cross section of FIG. 18 taken along the line A—A. In the drawings, an IC circuit, wires and the like formed in an SOI circuit are omitted and external contacting aluminum electrodes alone are shown as an electrode for contacting a capacitance, an electrode for as cillating the weight and the like in the sensor. In other words, all electrode contacting portions are formed on the major surface of the monocrystalline silicon substrate 101.

Figure 16:
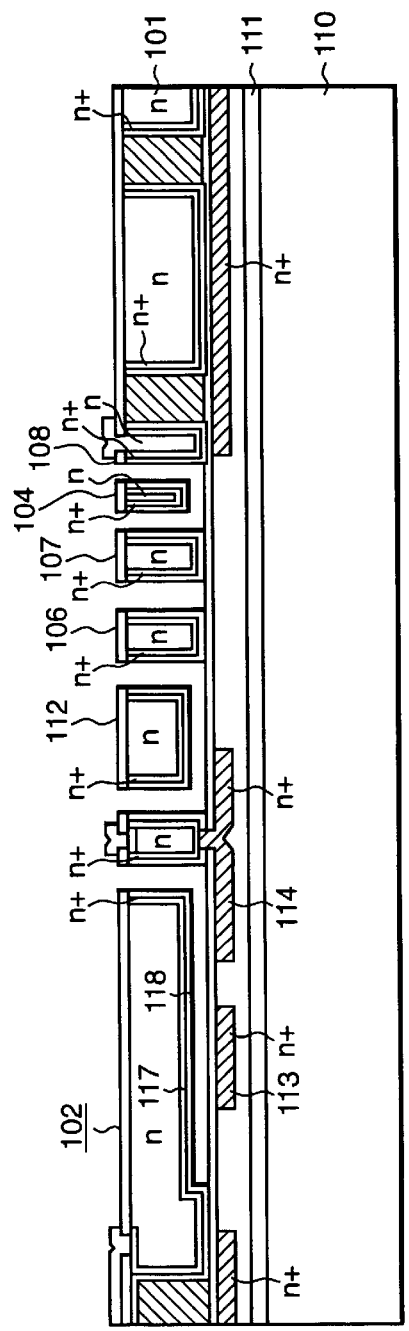
FIG. 16 is a cross-sectional view of a semiconductor mechanical sensor according to another embodiment of the present invention.

As shown in FIG. 16, the monocrystalline silicon substrate 101 is joined to a monocrystalline silicon substrate 110 through an SiO₂ film 111. In this monocrystalline silicon substrate 101, the beam structure described earlier is formed.

In FIGS. 16 and 18, in a surface of the weight 139 of the cantilever 102, a movable electrode 112 is formed. The movable electrode 112 includes the three projections 103, 104 and 105 of the weight 139. In addition, two electrodes 113 and 114 are formed below the weight 139. The excitation electrode 114 receives an alternating current electric power and excites the weight 139 by the static electricity. In short, the movable electrode 112 and the excitation electrode 114 form excitation electrodes.

The sense electrode 113 detects excitation of the weight 139, based on an output signal which is generated in response to excitation of the weight 139, and feedback control is performed to thereby achieve predetermined excitation of the weight 139. That is, the movable electrode 112 and the sense electrode 113 form electrodes for excitation feedback.

As shown in FIG. 18, on both sides of the projection 103 of the cantilever 102, fixed electrodes 133 and 134 (projection 106) are formed while on both sides of the projection 104, fixed electrodes 135 (projection 107) and 136 (projection 108) are formed. Further, on both sides of the projection 105, fixed electrodes 137 (projection 109) and 138 are formed. In other words, the projection 103 (movable electrode 112) and the fixed electrodes 133 and 134 form electrodes while the projection 104 (movable electrode 112) and the fixed electrodes 135 and 136 form electrodes. In addition, the projection 105 (movable electrode 112) and the fixed electrodes 137 and 138 form faced electrodes.

FIGS. 19 to 23 show manufacturing steps. In the following, the manufacturing steps will be described.

Figure 19:
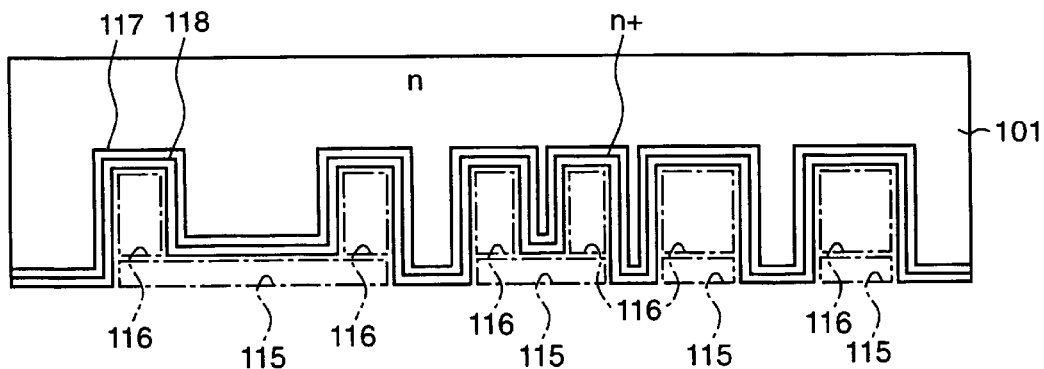

As shown in FIG. 19, an n type (100) monocrystalline silicon substrate 101 of 1 to 20 Ω·cm is prepared, and a recess portion 115 is etched in a major surface of the monocrystalline silicon substrate 101 by dry etching or wet etching to a predetermined depth, e.g., 0.1 to 5 μm. An SiO₂ film is formed on the major surface of the monocrystalline silicon substrate 101 and patterned by a photolithographic method. Following this, in the major surface of the monocrystalline silicon substrate 101 including the bottom portion of the recess portion 115, a trench 116 of a depth of about 0.1 to 30 μm is formed by dry etching or other suitable technique.

In this embodiment, a groove is formed by the recess portion 115 and the trench 116.

On the major surface of the monocrystalline silicon substrate 101 including an inner wall of the trench 116, an n⁺ type diffusion layer 117 is formed which will be then covered with an SiO₂ film 118 by thermal oxidation.

Figure 20:
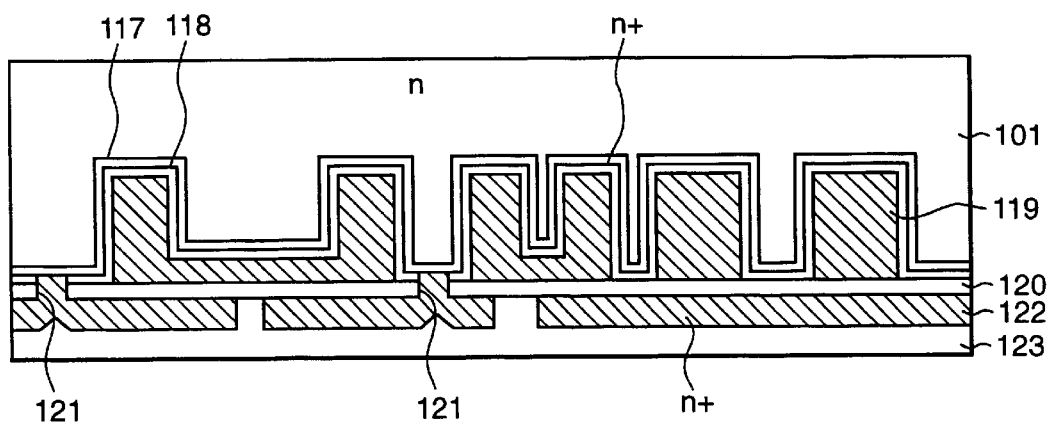

Following this, as shown in FIG. 20, a polysilicon film 119 is buried in the recess portion 115 and the trench 116 by an LPCVD method.

The surface of the polysilicon film 119 is then polished using the SiO₂ film 118 as a stopper to smooth the surface of the polysilicon film 119. At this stage, the surfaces of the polysilicon film 119 and the SiO₂ film 118 are preferably smoothed.

Then, in the surfaces, an SiO₂ film 120 is formed to a thickness of about 0.3 to 2 μm by a CVD method or other suitable method, and a bottom contact 121 is formed at a predetermined location for electrical connection with the n⁺ type diffusion layer 117.

Further, an n⁺ polysilicon 122 doped with As and P (phosphorus) is formed to a thickness of 0.2 to 1 μm which will serve as an electrode pattern and a shield layer.

Next, a BGSP film 123 which serves as an insulation film, for instance, is formed to a thickness of 0.2 to 1 μm in the surface. The surface of the BGSP film 123 is then polished and flattened.

Figure 21:
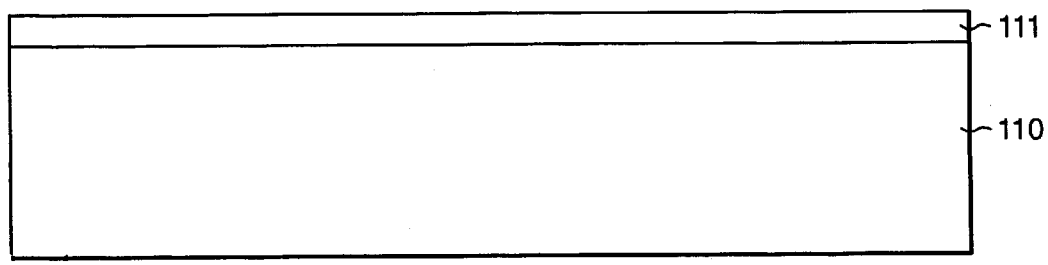

On the other hand, as shown in FIG. 21, a silicon substrate 110 is prepared and an SiO₂ film 111 is grown into a thickness 0.2 to 1 μm in a surface of the silicon substrate 110 by thermal oxidization.

Figure 22:
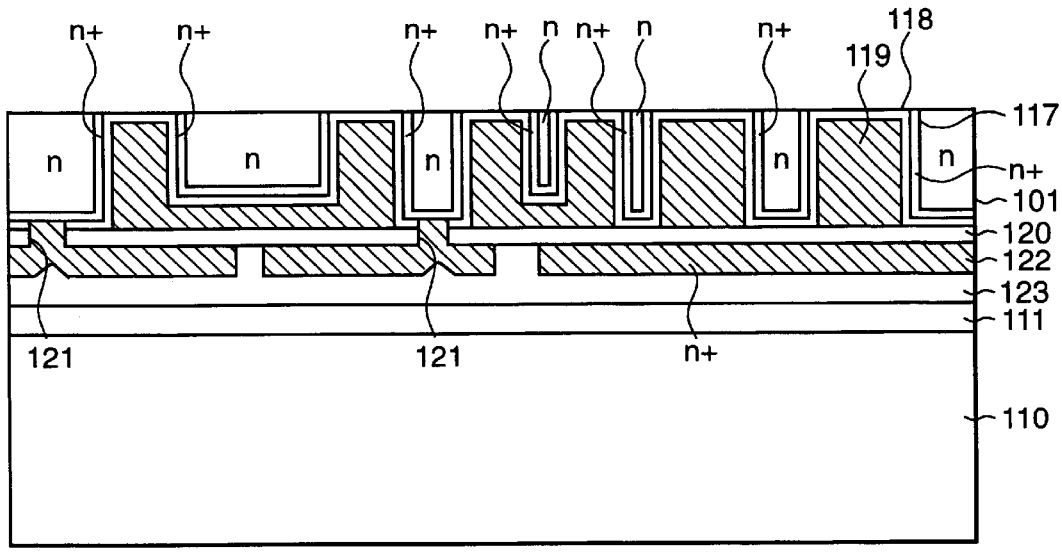

Following this, as shown in FIG. 22, the silicon substrates 101 and 110 are joined to each other through the SiO₂ film 111 within N₂ at a temperature of 1000° C., for instance. A back surface of the monocrystalline silicon substrate 101 is then selectively polished using the SiO₂ film 118 as a stopper. As a result, the polysilicon 119 and an isolated region of the silicon substrate 101 are exposed to the surface.

An IC board and other devices (not shown) are then formed in the region of the monocrystalline silicon substrate 101 by a known method, and an aluminum wire, a passivation film and a pad window (these elements are not shown) are formed as well.

Figure 23:
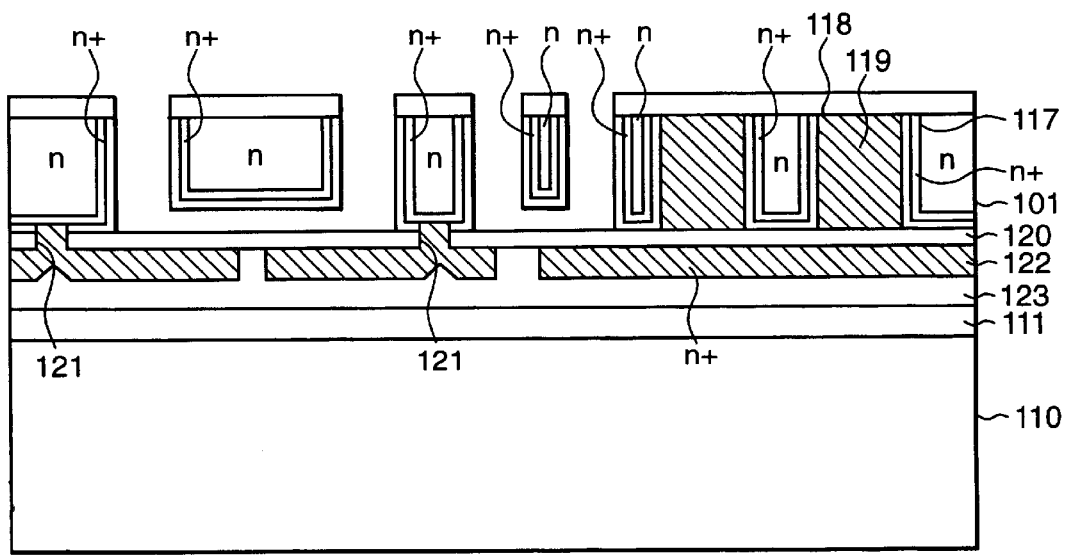

Next, as shown in FIG. 23, the SiO₂ film 118 is removed at a predetermined region, and the polysilicon film 119 is removed at a predetermined region using an etching hole 124 which is shown in FIG. 18. An etching solution may be TMAH (tetramethylammoniumhidroxide), for example. As a result of etching, a movable electrode (beam portion) is formed.

In the semiconductor mechanical sensor fabricated in this manner, the thin monocrystalline silicon substrate 101 is joined onto the monocrystalline silicon substrate 110 through the SiO₂ film 111, and in the monocrystalline silicon substrate 101, the cantilever 102 which has the weight 139 is formed at the tip. Further, in one surface of the weight 139 (the bottom surface in FIG. 16), the n⁺ type diffusion layer 117 is formed with the bottom surface of the monocrystalline silicon substrate 101 facing the surface of the weight, and the n⁺ type polysilicon 122 (excitation electrode 114) is formed so that the n⁺ type diffusion layer 117 and the n⁺ type polysilicon 122 form an excitation electrode. By applying an alternating current electric power to this excitation electrode, static electricity is created which excites the weight 139. In addition, in the axial direction which is perpendicular to the direction of the excitation of the weight 139, the n⁺ type diffusion layer 117 is formed in one surface of the weight 139 while the n⁺ type diffusion layer 117 is formed in a wall surface of the monocrystalline silicon substrate 101 facing the surface of the weight 139 so that the n⁺ type diffusion layer 117 of the weight 139 side and the n⁺ type diffusion layer 117 on the side of the wall surface of the monocrystalline silicon substrate 101 form a detecting electrode for detecting a change in a physical quantity. The physical quantity change detecting electrode detects a change in the electrical capacitance and hence a change in a physical quantity which acts in the same direction such as a yaw rate.

That is, an alternating current electric power is applied to the excitation electrode (i.e., the n⁺ type diffusion layer 117 and the n⁺ type polysilicon 122) to create static electricity and the weight is excited by the static electricity. Under this condition, the yaw rate detecting electrode (i.e., the n⁺ type diffusion layer 117 of the weight 139 side and the n⁺ type diffusion layer 117 on the side of the wall surface of the monocrystalline silicon substrate 101), for example, detects a change in an electrical capacitance in the axial direction which is perpendicular to the direction of the excitation of the weight 139, whereby a change in a physical quantity which acts in the same direction, such as a yaw rate, is detected.

Thus, in this embodiment, the recess portion 115 and the trench 116 are formed as a groove of a predetermined depth in the major surface of the monocrystalline silicon substrate 101 to thereby form the cantilever 102 which has the weight 139 (first step). In inner walls of the recess portion 115 and the trench 116 which surround a substrate surface region which serves as the weight 139 and the weight 139, a pair of electrodes are formed facing each other on the opposite sides of the trench 116 in the direction of the surface of the substrate (a left-to-right direction in FIG. 19), namely, the $n^+$ type diffusion layer 117. At the same time, in a substrate surface region which will serve as the weight 139, in the direction which is perpendicular to the direction of the surface of the substrate (up-to-down direction of FIG. 20; the direction of the thickness of the silicon substrate 101), the $n^+$ type diffusion layer 117 (first electrode) is formed (second step). Next, the recess portion 115 and the trench 116 are filled with a filling material, i.e., the polysilicon film 119, and the $n^+$ type polysilicon 122 (electrode) is formed on the opposite side of the polysilicon film 119 so as to face the $n^+$ type diffusion layer 117 (first electrode), followed by smoothing of the major surface of the monocrystalline silicon substrate 101 (third step). The major surface of the monocrystalline silicon substrate 101 and the silicon substrate 110 are then joined to each other (fourth step). Thereafter, the back surface side of the monocrystalline silicon substrate 101 is then polished by a predetermined amount to thereby make the monocrystalline silicon substrate 101 thin (fifth step). The polysilicon film 119 is then etched from the back surface side of the monocrystalline silicon substrate 101, whereby the cantilever 102 which has the weight 139 is formed (sixth step).

As a result, the semiconductor mechanical sensor comprises the thin monocrystalline silicon substrate 101 which is joined onto the monocrystalline silicon substrate 110 through the $SiO_2$ film 111 (insulation film), the cantilever 102 which is formed in the monocrystalline silicon substrate 101 and which has the weight 139, the movable electrode 112 which is formed in one surface of the weight 139 and a wall surface which corresponds to the same, the excitation electrode 114 (first electrode), the movable electrode 112 of the weight 139, the projections 103 to 105 which are formed one surface of the weight 139 and a wall surface which corresponds to the same in the axial direction which is perpendicular to the excitation electrode 114, and the fixed electrodes 133 to 138 (second electrode).

Either one of the electrodes, namely, the movable electrode 112 or the excitation electrode 114 is formed parallel to the major surface of the monocrystalline silicon substrate 101.

Further, all electrode contacting portions are formed on the same surface of the thin monocrystalline silicon substrate 101.

Thus, the semiconductor mechanical sensor comprises the thin monocrystalline silicon substrate 101 joined to the monocrystalline silicon substrate 110 through the $SiO_2$ film 111, the cantilever 102 which is formed in the monocrystalline silicon substrate 101 and which has the weight 139 at the tip, the excitation electrode which is formed in one surface of the weight 139 and a wall surface of the monocrystalline silicon substrate 110 facing the weight, the excitation electrode creating static electricity and exciting the weight when an alternating current electric power is applied thereto, and the detecting electrode which is formed in one surface of the weight 139 and a wall surface of the monocrystalline silicon substrate 110 facing the weight in the axial direction which is perpendicular to the direction of excitation of the weight 139, the detecting electrode detecting a change in an electrical capacitance and hence a change in a physical quantity which acts in the same direction.

In this manner, processes are performed stably and a device which is stable and accurate is manufactured without contamination by using a surface micro machining technique, without performing a thermal treatment and a photolithographic process during a wafer forming process, especially during fabrication of an IC circuit, in a condition where a wafer recess portion, a through hole and the like have been already formed.

Although the foregoing has described the present embodiment in relation to the case where the excitation electrode and the sense electrode are buried in the substrate, the sense electrode may be omitted to reduce cost, in which case, the silicon substrate as it is may be used as the excitation electrode, unlike the structure described above.

In addition, although the electrodes which are formed parallel to the wafer surface are used as the sense electrode and the excitation electrode and the electrodes which are disposed in the vertical direction are used as the fixed electrodes for detecting the Coriolis effect, in the present embodiment, the opposite is also possible. That is, one of the fixed electrodes which are disposed in the vertical direction in the silicon substrate 101 may be used as the excitation electrode, and the other one of the fixed electrodes may be used as the sense electrode for performing feedback, while the electrodes which are formed parallel to the wafer surface may be used as electrodes for detecting the Coriolis effect.

Further, as the polysilicon film 119 for filling the recess portion 115 and the trench 116 (i.e., a polycrystalline silicon film), an amorphous silicon film or a silicon film in which a polycrystalline portion and an amorphous portion are mixed may be used.

Next, still another example of the present invention will be described with reference to FIGS. 24 to 30.

This example is intended to further increase output as compared with the preceding example and to prevent destruction of the beam by excessive shock and the like.

FIGS. 24 to 30 show steps for manufacturing the sensor. In the following, the manufacturing steps will be described.

Figure 24:
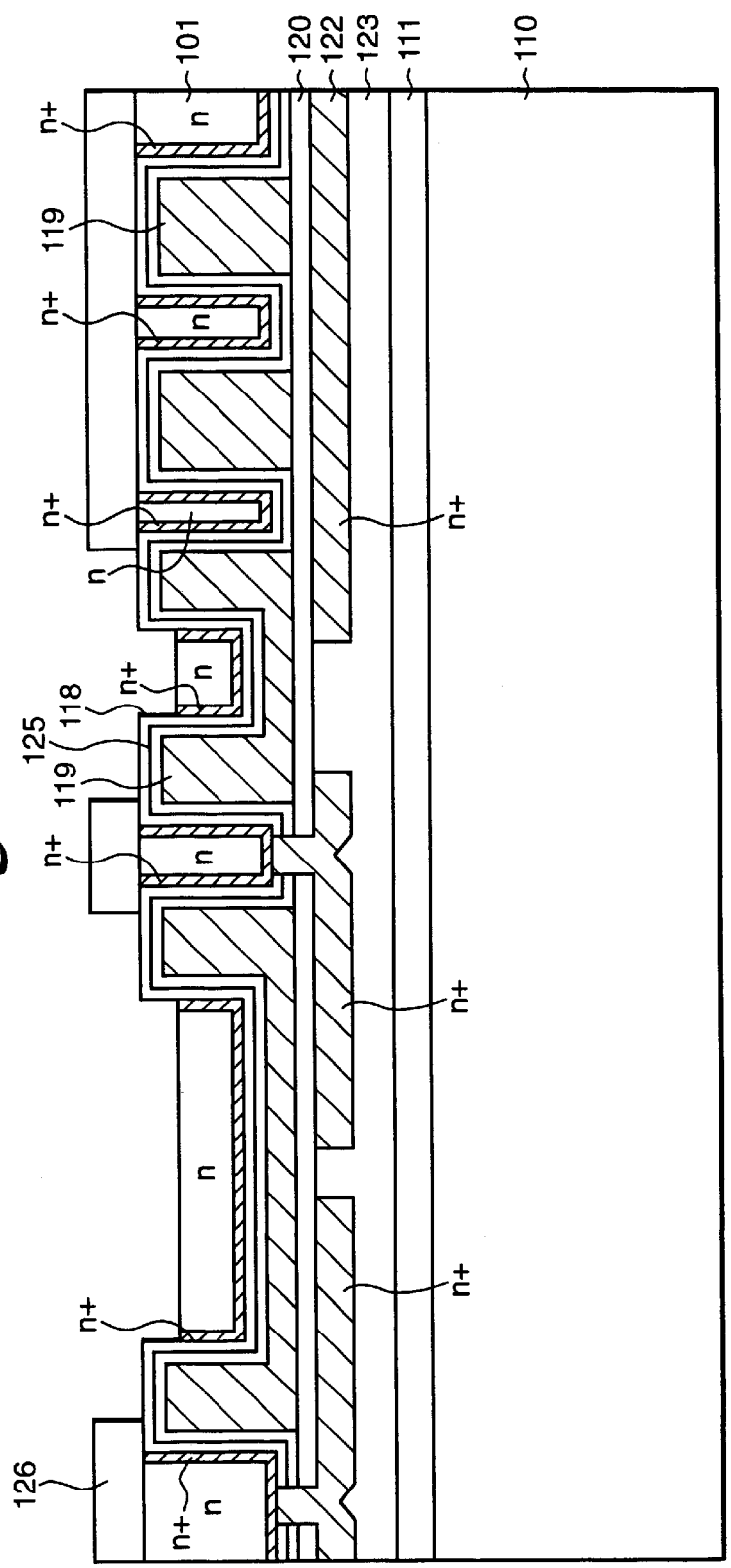

In the example of FIG. 19, as shown in FIG. 24, an $Si_3N_4$ film 125 having a thickness of 200 to 2000 Å is formed by the LPCVD method after formation of the $SiO_2$ film 118. In this example, the thickness of the $Si_3N_4$ film 125 is 500 Å.

In processes similar to those of the above example, polishing and flattening of the surface as shown in FIG. 22 in relation to the above example are performed.

Figure 25:
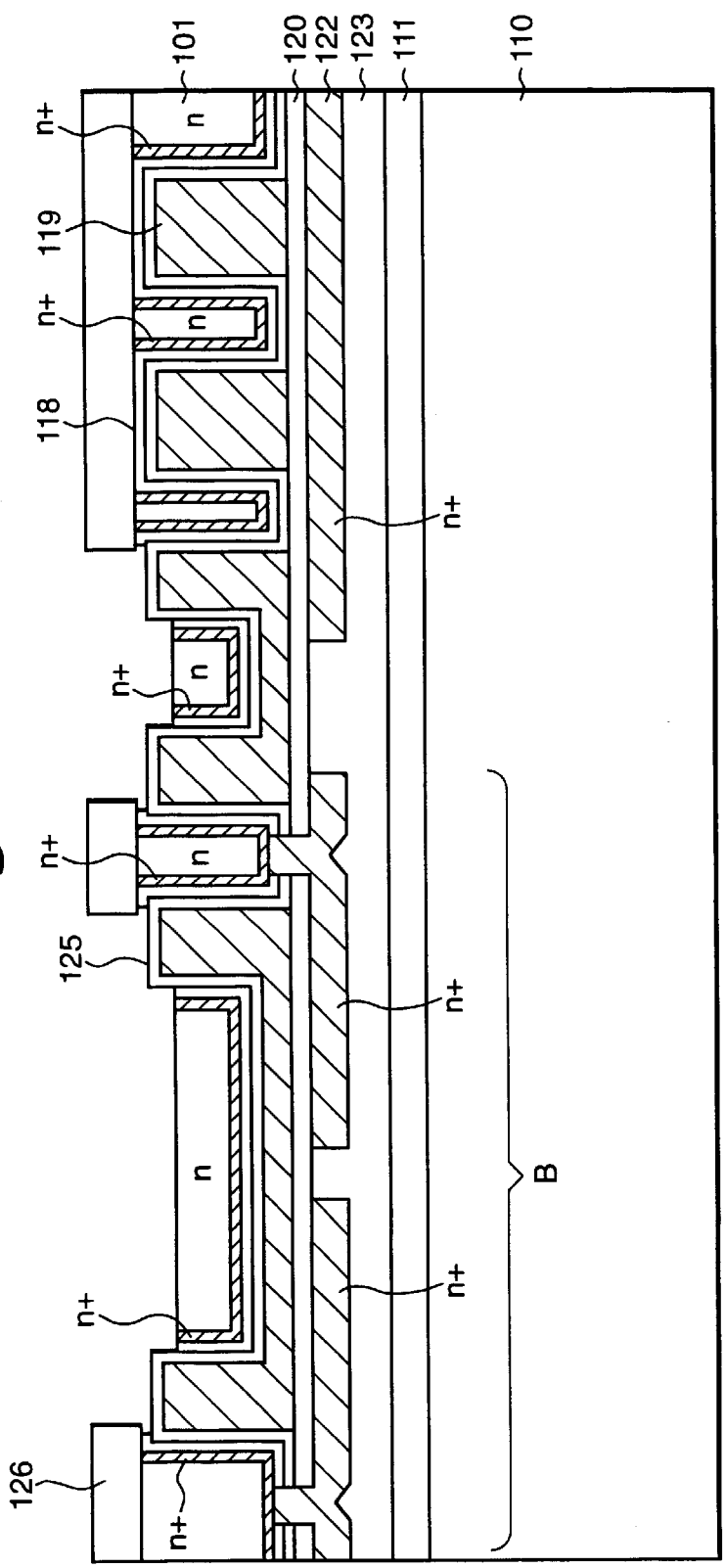

Following this, a resist 126 of FIG. 24 is patterned to a predetermined pattern by a photolithographic technique, and a region which will serve as the sense part of the monocrystalline silicon substrate 101 is removed by dry etching or other suitable method as shown in FIG. 25.

Next, using the resist 126 as a mask, the $SiO_2$ film 118 is removed by wet etching, for example, which primarily uses hydrofluoric acid as an etchant, followed by removal of the resist 126.

In the following, for clarity of explanation, an enlarged view of a portion of the sensor part B of FIG. 25 will be referred to.

Figure 26:
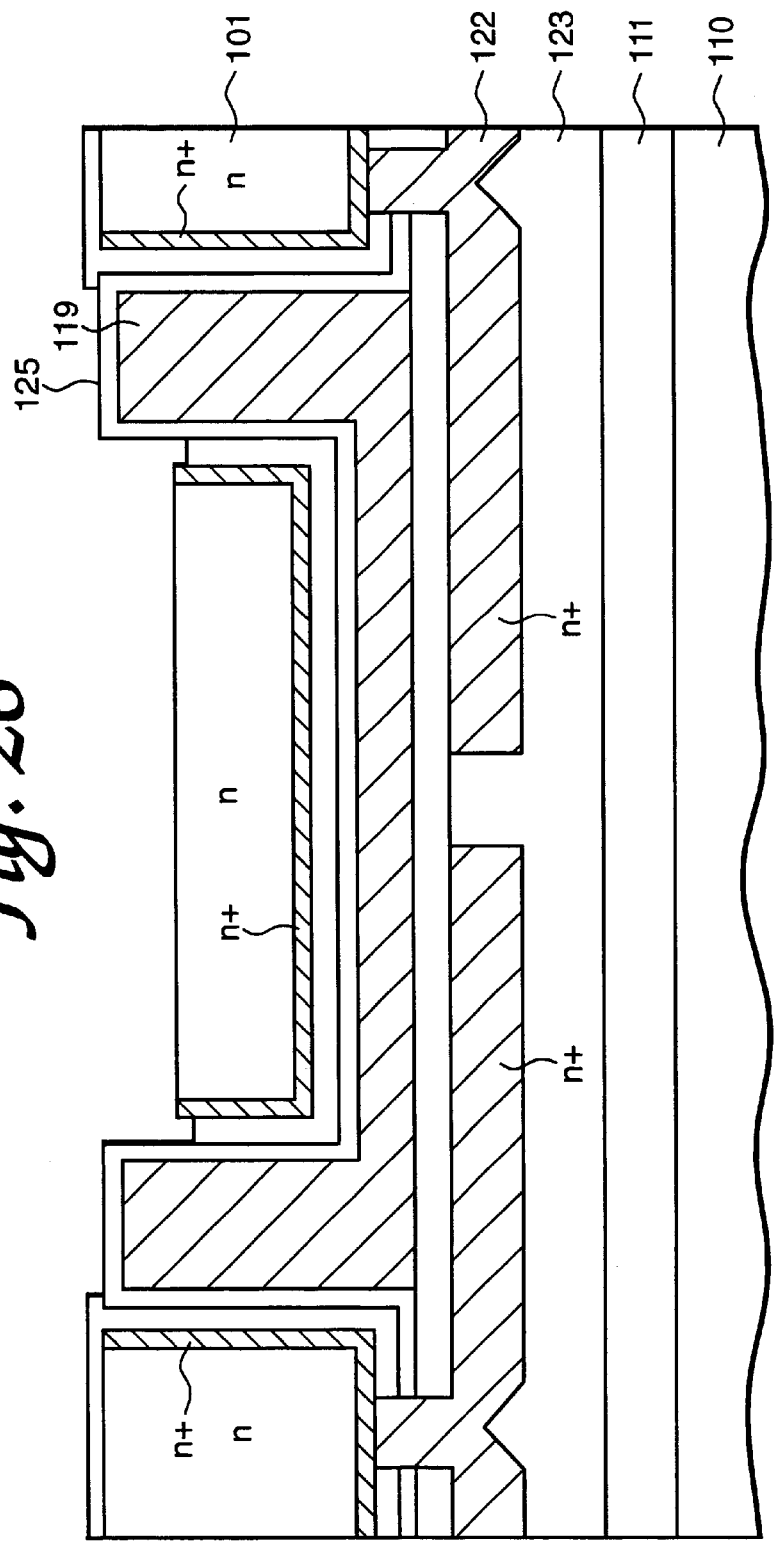

FIG. 26 shows the enlarged portion.

Figure 27:
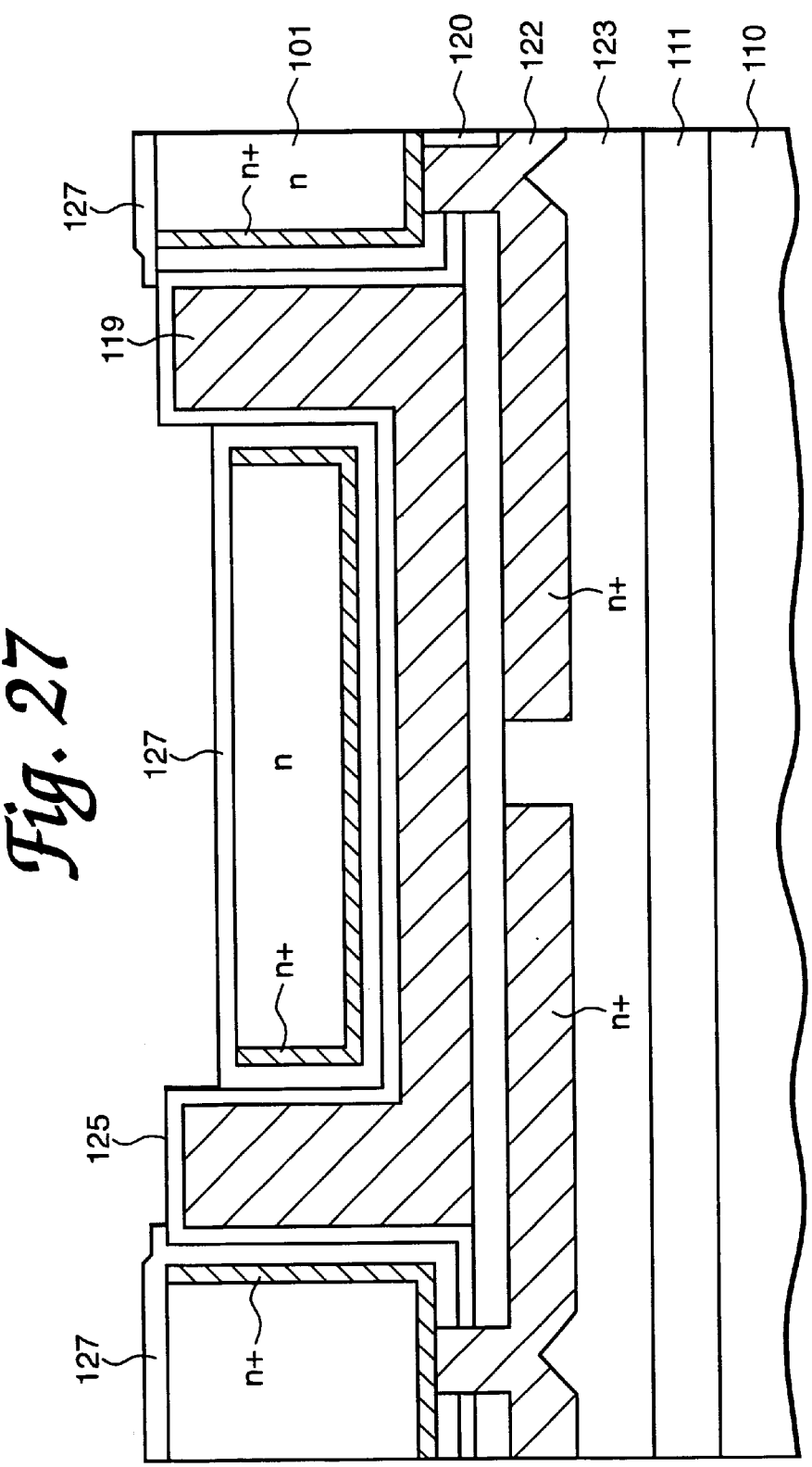

As shown in FIG. 27, using the $Si_3N_4$ film 125 as a mask, an $SiO_2$ film 127 is grown to a thickness of 500 to 10000 Å by thermal oxidation. In this embodiment, the thickness of the $SiO_2$ film 127 is 1000 Å.

Figure 28:
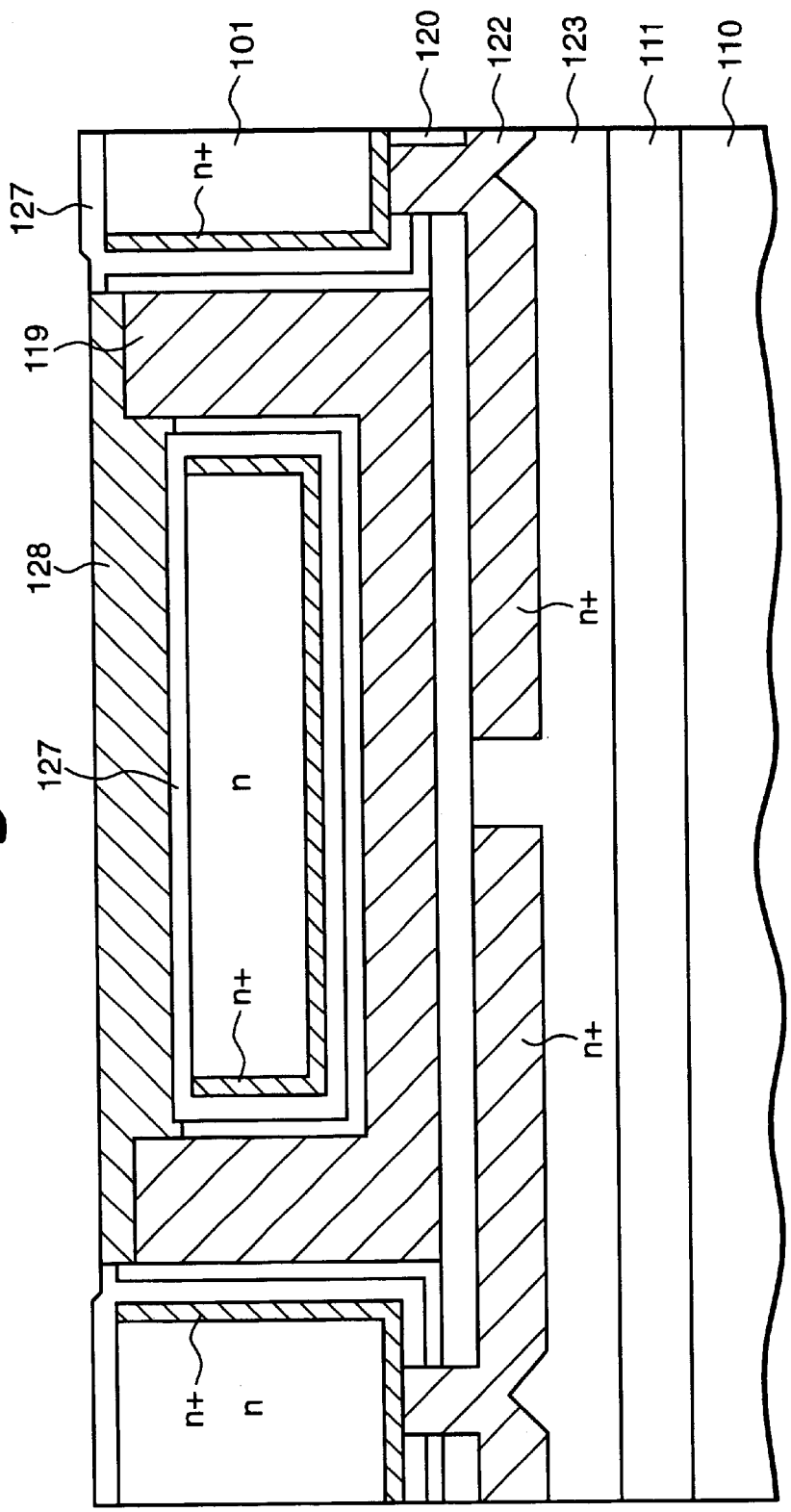

Next, as shown in FIG. 28, the $Si_3N_4$ film 125 used as a mask during thermal oxidation is removed by plasma etching or etching using heated phosphoric acid. A polysilicon 128 is then grown by the LPCVD method or other suitable method, on the surface. The surface of the polysilicon 128 is then selectively polished and removed using the $SiO_2$ film 127 as a stopper.

Further, the surface is treated with a TMAH (tetramethylammoniumhidroxide) solution. At this stage, in a peripheral portion, an IC circuit and the like are formed (not shown).

Figure 29:
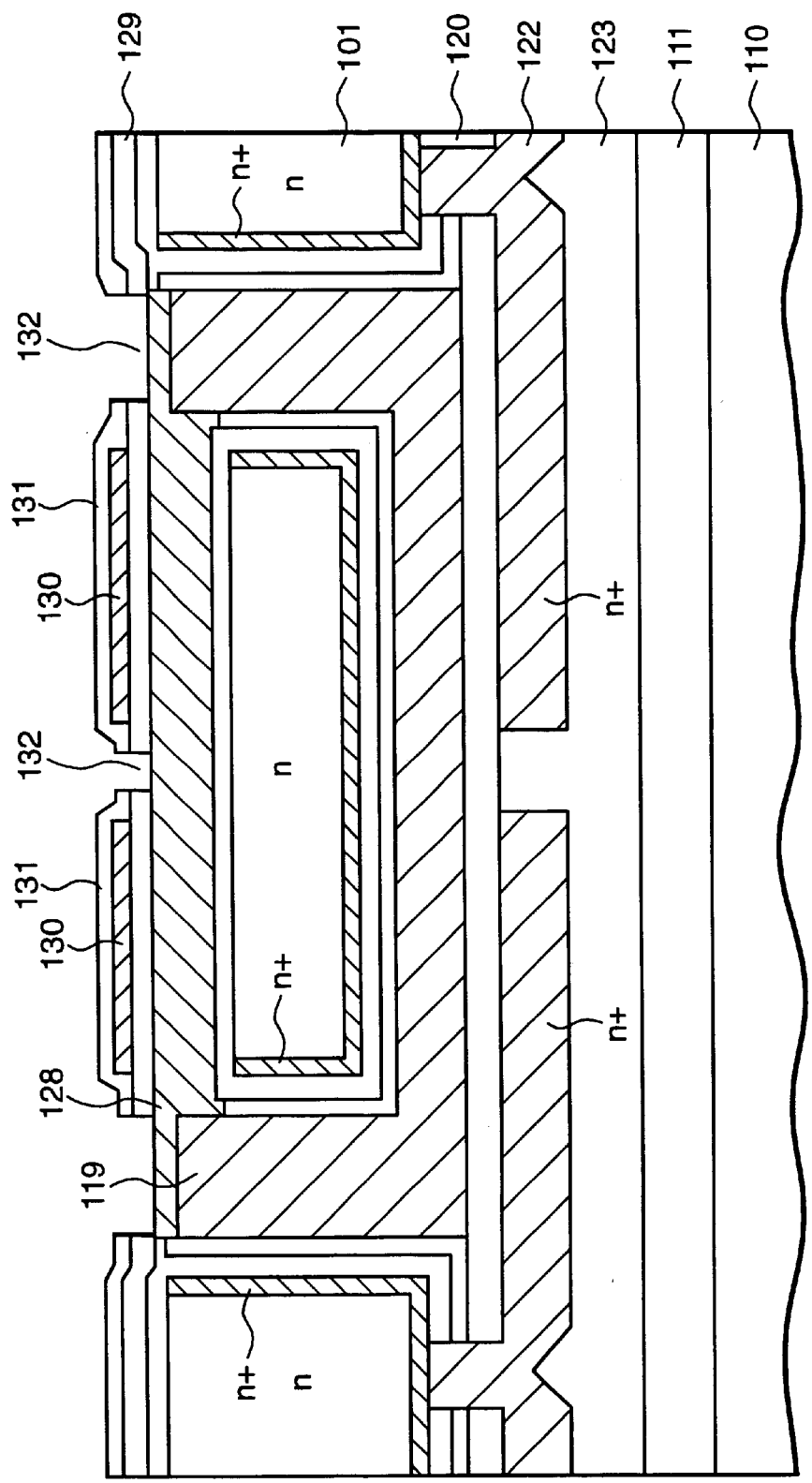

Thereafter, as shown in FIG. 29, an $Si_3N_4$ film 129 having a thickness of 500 to 2000 Å is formed on the surface, and an $n^+$ type polysilicon layer 130 is formed which will serve as a stopper against excessive amplitudes of the electrode layer and the sensor. Following this, a BPSG film 131 is formed as a surface protection film. This film may be formed by an $Si_3N_4$ film or the like. A window portion 132 is then formed.

Figure 30:
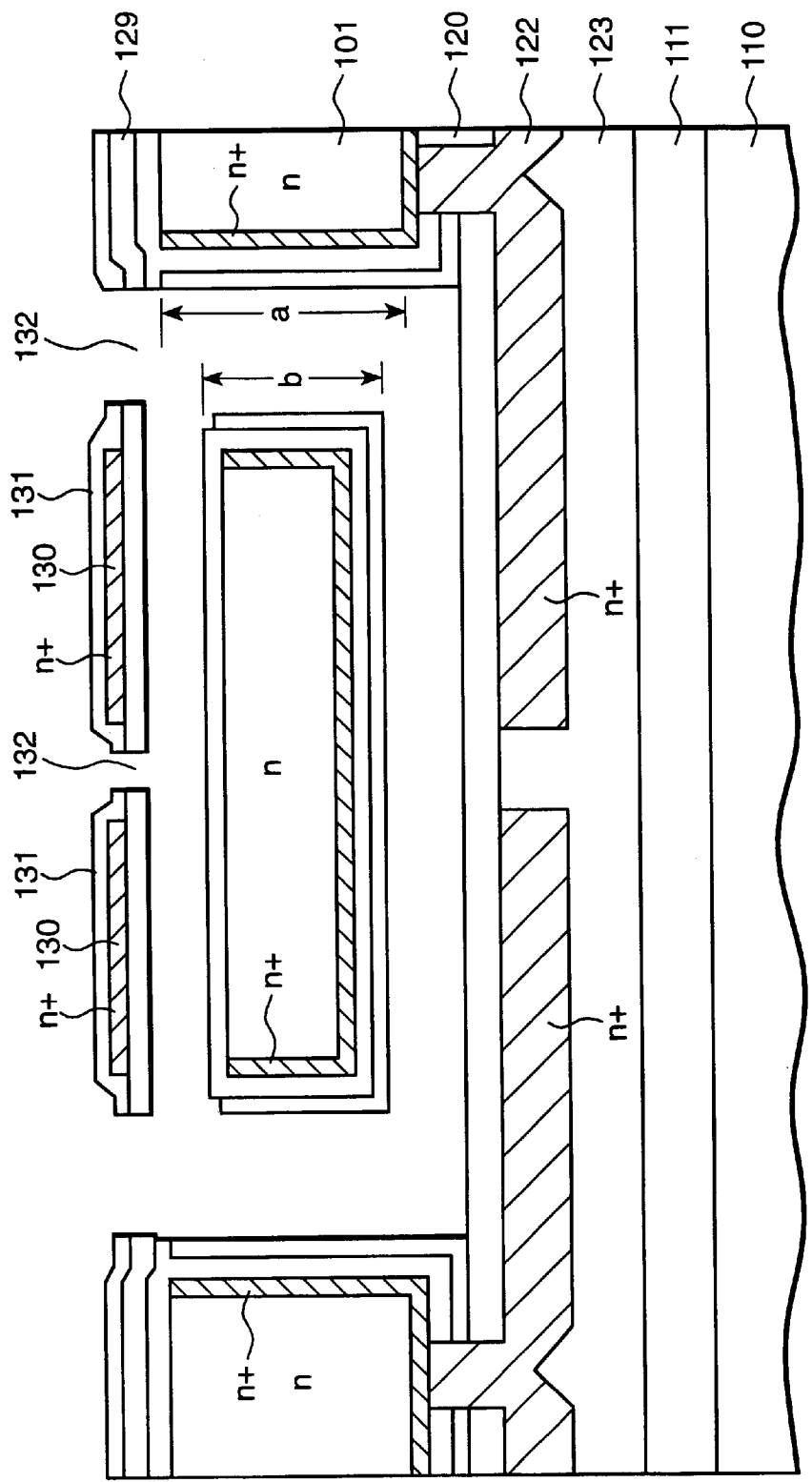

Then, as shown in FIG. 30, the polysilicon 119 and the polysilicon 128 are etched through the window portion 132 with the TMAH solution.

In this manner, a sensor which comprises a movable portion (cantilever) which is entirely surrounded by an electrode and a stopper is obtained. In such a structure, when the weight portion is excited in a direction which is perpendicular to the substrate, as shown in FIG. 30, since a>b and b is within the range of a, there will be almost no capacitance change created during detection of a yaw rate due to excitation. The relation a>b is attainable in the first embodiment as well.

FIG. 31 is a view which clearly shows more detail of the overall structure.

As described above, in the present example, since the stopper member 130 is disposed above the cantilever 102, output is further increased, as compared with the above example, and destruction of the cantilever by excessive shock and the like is prevented.

That is, in the present example, in the first step, a groove of a predetermined depth is formed in the major surface of the monocrystalline silicon substrate to thereby form the beam which has the weight. In the second step, a pair of electrodes are formed which faced each other on the opposite sides of the groove in a substrate surface region and an inner wall of the groove which surrounds the weight in the direction of the surface of the substrate, while the first electrode is formed in a substrate surface region which will serve as the weight in a direction which is perpendicular to the surface of the substrate. In the third step, the groove is filled with a filling material and an electrode which faces the first electrode through the filling material is formed, and the major surface of the monocrystalline silicon substrate is smoothed. Next, in the fourth step, the major surface of the monocrystalline silicon substrate and the silicon substrate are joined to each other. In the fifth step, the back surface side of the monocrystalline silicon substrate 101 is polished by a predetermined amount to thereby make the monocrystalline silicon substrate thin. Lastly, in the sixth step, the filling material is etched from the back surface side of the monocrystalline silicon substrate, whereby the beam which has the weight is formed. As a result, the semiconductor mechanical sensor according to the present invention is completed.

It is to be noted that the present invention is not limited to the embodiments described above. Rather, two pairs of the sensor units may be arranged in directions perpendicular to each other in order to detect yaw rates in the two axial directions. Further, the present invention is not limited to a cantilever. The present invention is also not limited to detection of a yaw rate. For instance, the excitation electrode of the embodiments above may be replaced with an electrode which detects a capacitance of displacement in an up-to-down direction so that the present invention is applied to a mechanical sensor which is capable of detecting displacements in two directions.

As heretofore described in detail, the present invention creates effects by which a yaw rate sensor of the beam excitation type capacity detection method and a method of manufacturing the same are obtained, and a semiconductor mechanical sensor which can detect movement in two or three directions and a method of manufacturing the same are obtained.

What is claimed is:

1. A semiconductor mechanical sensor comprising:
   a supporting substrate;
   a beam structure of semiconductive material having a geometry that a thickness thereof is greater than a width thereof;
   a vibrating member to vibrate said beam structure with respect to a surface of said supporting substrate; and
   a detecting electrode portion to detect a displacement of said beam structure according to a mechanical force acting upon said beam structure in a perpendicular direction along a vibration of said beam structure by said vibrating member.

2. A semiconductor mechanical sensor device, wherein a plurality of semiconductor mechanical sensors as defined by claim 1 are arranged monolithically.

3. A semiconductor mechanical sensor according to claim 1, wherein said supporting substrate comprises monocrystalline silicon.

4. A semiconductor mechanical sensor according to claim 1, wherein said beam structure comprises a first portion forming a pair of first capacitive electrodes in association with said vibrating member, a second portion forming a pair of second capacitive electrodes in association with said detecting electrode portion, a fixed portion fixing said beam structure to said supporting substrate and a support portion intermediately supporting said first and second portions to said fixed portion.

5. A semiconductor mechanical sensor according to claim 1, wherein said vibrating member includes a vibration electrode which is disposed between said supporting substrate and said beam structure to be spaced from said beam structure.

6. A semiconductor mechanical sensor according to claim 5, wherein said vibration electrode is stationary disposed on said supporting substrate with an insulating layer interposed therebetween.

7. A semiconductor mechanical sensor according to claim 6, wherein said vibration electrode comprises a doped polycrystalline silicon.

8. A semiconductor mechanical sensor according to claim 5, wherein said vibrating member includes a vertical portion connected to said vibration electrode for electrically conducting between said vibration electrode and an external part.

9. A semiconductor mechanical sensor according to claim 8, wherein said vertical portion comprises monocrystalline silicon and is isolated from said supporting substrate by means of an insulating layer.

10. A semiconductor mechanical sensor according to claim 4, wherein a comb-teeth-like structure is so formed on said beam structure that each tooth of said comb-teeth-like structure functions as said second portion of said beam structure, and corresponding detecting electrode portions are stationary provided over said supporting substrate, thereby plural pairs of said second capacitive electrodes are integrated on said beam structure.

11. A semiconductor mechanical sensor according to claim 1, wherein said detecting electrode portion comprises a detection electrode which is isolated from said supporting substrate by means of an insulating layer.

12. A semiconductor mechanical sensor according to claim 11, wherein said detecting electrode portion comprises monocrystalline silicon and said detection electrode comprises a high impurity concentration region.

13. A semiconductor mechanical sensor according to claim 4, wherein said fixed portion is fixed to said supporting substrate through an insulating layer.

14. A semiconductor mechanical sensor according to claim 13, wherein said first and second portions, said support portion and said fixed portion comprise monocrystalline silicon.

15. A semiconductor mechanical sensor according to claim 1, wherein said beam structure comprises monocrystalline silicon, and is isolated from said supporting substrate by means of an insulating layer.

16. A semiconductor mechanical sensor according to claim 15, wherein said beam structure has a high impurity concentrating region disposed to encompass sidewalls and bottom of said beam structure.

17. A semiconductor mechanical sensor according to claim 16, wherein said high impurity concentration region of said beam structure is covered with an insulation film.

18. A semiconductor mechanical sensor comprising:

a layer of a silicon material which is used as a conductive material;

a substrate provided on the lower side of said layer and electrically insulated from the layer;

said layer including;

a beam structure having a first weight portion forming a first capacitive electrode for first displacement in a parallel direction to a surface of said substrate, a second weight portion forming a second capacitive electrode for second displacement in a perpendicular direction to said first displacement, a fixed portion for fixing said beam structure to said substrate and a support portion for intermediately supporting said first and second weight portions to said fixed portion, an insulating groove extending through a thickness of said layer around the entire periphery of said beam structure, and a first stationary block capacitively coupling with said first capacitive electrode, said first stationary block being defined by said insulating groove on the outer side of said beam structure to face said first weight portion separately across said insulating groove and being fixed to said substrate; and gap means forming a gap space in order to space said first and second weight portions and said support portion from a surface of said second substrate, said substrate being separated from said layer by an insulating layer which is at least provided on the lower side of said fixed portion and said first stationary block.

19. A semiconductor mechanical sensor according to claim 18, wherein a width of said support portion is smaller than a thickness of said fixed portion.

20. A semiconductor mechanical sensor according to claim 18, wherein said layer is formed of a n-type silicon material.

21. A semiconductor mechanical sensor according to claim 18, wherein said substrate is formed of a silicon material having a surface covered with an insulating oxidation film.

22. A semiconductor mechanical sensor according to claim 18, further comprising a driving electrode member facing said second weight portion for producing an electrostatic force for said beam structure and causing said second displacement of said beam structure.

23. A semiconductor mechanical sensor according to claim 22, wherein said driving electrode member is provided on a lower side of said second weight portion of said beam structure.

24. A semiconductor mechanical sensor according to claim 23, wherein said insulating layer is further provided on the lower side of said driving electrode member.

25. A semiconductor mechanical sensor according to claim 23, wherein said layer further includes a second stationary block electrically connected to said driving electrode member, said second stationary block being defined by said insulating groove on the outer side of said beam structure separately across said insulating groove and being fixed to said substrate, and wherein said insulating layer is further provided on the lower side of said second stationary block.

26. A semiconductor mechanical sensor according to claim 18, wherein said beam structure has a high impurity concentration region disposed to encompass sidewalls and bottom of said beam structure.

27. A semiconductor mechanical sensor according to claim 26, wherein said high impurity concentration region of said beam structure is covered with an insulation film.

28. A semiconductor mechanical sensor comprising:

a supporting substrate;

a beam structure which includes a first weight portion forming a first capacitive electrode on a side surface of said first weight portion, a fixed portion for fixing said beam structure to said supporting substrate and a thin support portion for intermediately connecting between said first weight portion and said fixed portion;

a first stationary block arranged on a side of said beam structure to face said first capacitive electrode separately across an air gap, and fixed to said supporting substrate;

gap means for forming a gap space in order to space said first weight portion and said thin support portion from a surface of said supporting substrate, whereby said first weight portion may be displaced in a parallel direction to the surface of said supporting substrate according to the degree of mechanical force applied thereon;

an electrode line conveying an electrical signal for said semiconductor mechanical sensor, and provided on a lower side of said beam structure; and a second stationary block electrically connected to said electrode line, said second stationary block being fixed to said supporting substrate to be arranged on a outer side of said beam structure and isolated from said first stationary block, said beam structure and said first and second stationary blocks being formed of a silicon material which is used as a conductive material and electrically insulated from said supporting substrate.

29. A semiconductor mechanical sensor according to claim 28, wherein said electrode line is provided with a signal for producing an electrostatic force for said beam structure and causing a vibration of said beam structure.

30. A semiconductor mechanical sensor according to claim 28, wherein said beam structure has a high impurity concentration region disposed to encompass sidewalls and bottom of said beam structure.

31. A semiconductor mechanical sensor according to claim 30, wherein said high impurity concentration region of said beam structure is covered with an insulation film.

* * * * *

UNITED STATES PATENT AND TRADEMARK OFFICE
CERTIFICATE OF CORRECTION

PATENT NO. : 6,227,050 B1 Page 1 of 1
DATED : May 8, 2001
INVENTOR(S) : Fujii et al.

It is certified that error appears in the above-identified patent and that said Letters Patent is hereby corrected as shown below:

<u>Title page,</u>
Please change item "[73] Assingee: Nippondense Co., Ltd., Kariya (JP)" to
-- [73] Assingee: DENSO Corporation, Kariya (JP) --

Signed and Sealed this

Thirtieth Day of March, 2004

JON W. DUDAS
*Acting Director of the United States Patent and Trademark Office*